(12) United States Patent
Wu et al.

(10) Patent No.: US 11,433,168 B2
(45) Date of Patent: Sep. 6, 2022

(54) DUAL CHAMBER GAS EXCHANGER AND METHOD OF USE FOR RESPIRATORY SUPPORT

(71) Applicants: UNIVERSITY OF MARYLAND, BALTIMORE, Baltimore, MD (US); BREETHE, INC, Halethorpe, MD (US)

(72) Inventors: Zhongjun Wu, Marriottsville, MD (US); Bartley P. Griffith, Gibson Island, MD (US); Jiafeng Zhang, Silver Spring, MD (US); Steven J. Orwig, Bowie, MD (US)

(73) Assignees: UNIVERSITY OF MARYLAND, BALTIMORE, Baltimore, MD (US); BREETHE, INC., Halethorpe, MD (US)

(*) Notice: Subject to any disclaimer, the term of this patent is extended or adjusted under 35 U.S.C. 154(b) by 0 days.

(21) Appl. No.: 16/791,117

(22) Filed: Feb. 14, 2020

(65) Prior Publication Data

US 2020/0206404 A1    Jul. 2, 2020

Related U.S. Application Data

(63) Continuation of application No. PCT/US2018/000133, filed on Aug. 15, 2018.

(Continued)

(51) Int. Cl.
*A61M 1/16* (2006.01)
*A61M 1/36* (2006.01)
*A61M 60/113* (2021.01)

(52) U.S. Cl.
CPC ........ *A61M 1/1698* (2013.01); *A61M 1/1629* (2014.02); *A61M 1/3607* (2014.02);
(Continued)

(58) Field of Classification Search
CPC ............. A61M 1/1629; A61M 1/1698; A61M 1/3607; A61M 60/113; A61M 2202/0225; A61M 2206/20
See application file for complete search history.

(56) References Cited

U.S. PATENT DOCUMENTS 5,270,005 A    12/1993  Raible
5,346,621 A     9/1994  Haworth et al.
(Continued)

FOREIGN PATENT DOCUMENTS

JP    2001079083    3/2001
WO    2009/098457   8/2009
WO    2016/181189   11/2016

OTHER PUBLICATIONS

Intenrational Search Report issued in co-pending application No. PCT/US18/00133 dated Jan. 16, 2019.
(Continued)

*Primary Examiner* — Benjamin J Klein
(74) *Attorney, Agent, or Firm* — Whiteford, Taylor & Preston, LLP; Gregory M. Stone

(57) ABSTRACT

The device of the present invention includes a dual chamber gas exchanger that is configured for increased flexibility and scalability for many clinical applications. The dual chamber oxygenator can be configured and used in various applications, such as in a heart-lung machine for cardiopulmonary support during cardiothoracic surgery, in an extracorporeal membrane oxygenation (ECMO) circuitry, as a respiratory assist device for patients with lung failure, and the like. The dual chamber gas exchanger features two sweep gas flow paths and two gas exchange membrane bundles enclosed in a housing structure with various blood flow distribution and gas distribution mechanisms. The gas exchanger includes an outer housing, an intermediate housing, two gas exchange
(Continued)

fiber bundles, a blood inlet, a blood outlet, two gas inlets, two gas outlets, two gas distribution chambers and an optional heat exchanger.

24 Claims, 26 Drawing Sheets

Related U.S. Application Data

(60) Provisional application No. 62/545,512, filed on Aug. 15, 2017.

(52) U.S. Cl.
CPC ... *A61M 60/113* (2021.01); *A61M 2202/0225* (2013.01); *A61M 2206/20* (2013.01)

(56) References Cited

U.S. PATENT DOCUMENTS

| | | | |
|---|---|---|---|
| 5,578,267 A * | 11/1996 | Cosentino | A61M 1/1629 422/46 |
| 5,817,278 A * | 10/1998 | Fini | B01D 63/026 424/44 |
| 5,855,201 A | 1/1999 | Yasuhiro et al. | |
| 6,998,093 B1 | 2/2006 | McIntosh et al. | |
| 7,871,566 B2 | 1/2011 | Strauss et al. | |
| 7,927,544 B2 | 4/2011 | Federspiel et al. | |
| 8,518,259 B2 | 8/2013 | Cloutier et al. | |
| 8,529,834 B2 | 9/2013 | Johns | |
| 8,545,754 B2 | 10/2013 | Carpenter | |
| 8,709,343 B2 | 4/2014 | Thomas | |
| 8,795,220 B2 | 8/2014 | Reggiani et al. | |
| 9,278,168 B2 | 3/2016 | Gellman et al. | |
| 9,320,844 B2 | 4/2016 | Joost et al. | |
| 2013/0094997 A1 | 4/2013 | Wang et al. | |
| 2013/0209314 A1 * | 8/2013 | Roller | A61M 1/1698 422/46 |
| 2013/0296633 A1 | 11/2013 | Strueber | |
| 2013/0343954 A1 * | 12/2013 | Gartner | A61M 60/113 422/48 |
| 2016/0296685 A1 | 10/2016 | Wu et al. | |
| 2016/0331882 A1 * | 11/2016 | Saito | A61M 1/1629 |
| 2018/0126057 A1 * | 5/2018 | Steffens | A61M 1/1698 |

OTHER PUBLICATIONS

European Search Report issued in co-pending application No. 18845595.0 dated May 27, 2021.

* cited by examiner

DUAL CHAMBER GAS EXCHANGER AND METHOD OF USE FOR RESPIRATORY SUPPORT

CROSS-REFERENCES TO RELATED APPLICATION

This application is a continuation of international patent application PCT/US2018/000133, filed on Aug. 15, 2018, which claims the benefit of provisional patent application 62/545,512, filed on Aug. 15, 2017, the full disclosure of which is incorporated herein by reference.

STATEMENT ON GOVERNMENT INTEREST

This invention was made with government support under Grant Number HL118372 awarded by the National Institutes of Health. The government has certain rights in the invention.

BACKGROUND OF THE INVENTION

1. Field of the Invention

The present invention relates generally to medical devices and methods. More particularly, the present invention relates to devices for extracorporeal membrane oxygenation, respiratory support, and cardiopulmonary support.

Oxygenating blood with artificial devices began in the 1930s. Early blood oxygenators, such as thin film blood oxygenators and bubble oxygenators, were based on exposing blood directly to oxygen or air. Direct contact of blood with oxygen is an effective way of exchanging gases, but it also damages the blood's proteins and formed elements. Thus, these earlier blood oxygenators could only be used for limited time, such as for a few hours.

Other approaches, such as gas-permeable solid membranes, separated the blood from sweep gas to eliminate damage caused by direct blood and gas contact. Solid membranes were the basis for many design platforms, but were hindered by manufacturing challenges and thrombogenicity. Thus, hollow fiber membranes emerged. Hollow fiber membranes enabled the design and construction of efficient and small blood oxygenators with low prime volume, increased ratio of gas-exchange surface area to blood volume, and reduced thrombogenicity. Many current blood oxygenators include hollow fibers of microporous materials.

Many types of blood oxygenators based on hollow fiber membrane materials have been designed and developed. Oxygenators with hollow fiber membranes typically include a single chamber with one fiber bundle and are characterized by the blood flow path within the fiber bundles. For example, four types of blood flow paths are (1) longitudinal (axial) flow through an annular bundle; (2) circumferential flow around an annular bundle; (3) transverse flow across a bundle of substantially rectangular cross-section; and (4) radial flow through an annular bundle.

Although the membrane blood oxygenators based on the above principles are generally acceptable for cardiopulmonary bypass during open-heart surgeries, they have a number of problems when they are used for respiratory support over longer durations (days to weeks). For example, typical hollow fiber membrane blood oxygenators have relatively large blood-contacting surface areas, large prime volume, large physical sizes with very limited long-term biocompatibility and durability, and limited flexibility for various clinical applications. Patients on respiratory support with these current blood oxygenators are often bedridden with limited mobility due to complexity and bulky size of the typical blood oxygenators caused by the inherent blood fluid dynamics. Further complications are caused by non-uniform blood flow through the fiber membranes and laminar boundary flow zones between blood cells and fiber membranes.

Non-uniform blood distribution can cause many problems in hollow fiber membrane blood oxygenators, such as hyper- and hypo-perfusion of the blood in the flow path. Hyperperfusion does not have any additional benefits relative to oxygen-saturated blood. However, hypo-perfusion can be detrimental to the patient. Hollow fiber membrane blood oxygenators use long flow paths to increase the blood contact with the larger fiber membrane surface area to ensure that all blood cells in hypo-perfusion regions are well-oxygenated. However, large gas exchange membrane surface areas and large prime volume provide poor biocompatibility and wearability. Non-uniform blood flow can also induce excessive mechanical shear stresses or stasis in the blood flow path in oxygenators. These are the major contributing factors to blood activation and thrombosis formation, resulting in limited long-term biocompatibility and durability.

In addition to these technical issues, typical hollow fiber membrane blood oxygenators lack flexibility for various clinical applications. Often, one device only serves for one application, which may be insufficient for some patients. These oxygenators often have limited capability for removing carbon dioxide while transferring oxygen to some patients. Moreover, high sweep gas flow rates are required to remove carbon dioxide, or blood flow rates must remain low because of limited sweep gas flow rates (e.g., in ambulatory use). Low blood flow rates can result in thrombosis forming inside oxygenators.

In various clinical applications, such as in a hospital, ambulatory, or home setting, the requirement for and availability of the sweep gas can vary. In particular, oxygen sources can be a challenge in ambulatory applications, such as when a bulky oxygen tank or a large heavy oxygen concentrator is required. Thus, typical blood oxygenators can limit patient mobility and flexibility.

Removing carbon dioxide from the oxygenator typically requires higher flow rates and a gas that is nearly free of carbon dioxide. Oxygen is a typical primary sweep gas to deliver oxygen and remove carbon dioxide. For example, at a sweep gas flow rate of 1:1 to blood flow rate, only 5% (50 cc/liter) of the oxygen is delivered to the circulating blood. However, increasing carbon dioxide removal requires the sweep gas to blood flow rate ratio above 1:1. Thus, the percentage of oxygen utilization is much less than 5% and the efficiency of oxygen delivery is extremely poor and costly. Even in an acute setting at 5 liters/min over a 24-hour period a patient would consume 7,200 liters of oxygen with less than 5% being delivered to the patient. Room air at high flow rates can also be a sufficient sweep gas to remove carbon dioxide. Current oxygenators have limited adjustability and therefore lack precise control of oxygen delivery and carbon dioxide removal.

Thus, it can be seen that there is a need for improved oxygenators that efficiently use sweep gases for gas exchange. Such an oxygenator can serve various applications and patients.

2. Background of the Invention

Relevant background patents include: US Patent Publ. No. 2013/0296633; U.S. Pat. Nos. 9,320,844; 8,709,343; 8,529,834; 7,871,566; 5,270,005; 8,795,220; 8,545,754; 8,518,259; and 6,998,093.

BRIEF SUMMARY OF THE INVENTION

The device of the present invention includes a gas exchanger that is configured for increased flexibility and scalability for many clinical applications. The gas exchanger can be configured and used in various applications, such as in a heart-lung machine for cardiopulmonary support during cardiothoracic surgery, in an extracorporeal membrane oxygenation (ECMO) circuitry, as a respiratory assist device for patients with lung failure, and the like. In some embodiments, the dual chamber gas exchanger features two sweep gas flow paths. In other embodiments, two gas exchange membrane bundles are enclosed in a housing structure that provides two chambers that isolate the gas flow and provide for sequential blood flow with various blood flow distribution and gas distribution mechanisms. In some embodiments, the gas exchanger includes an outer housing, an intermediate housing, two gas exchange fiber bundles, a blood inlet, a blood outlet, two gas inlets, two gas exhausts or outlets, two gas distribution chambers and an optional heat exchanger. In particular embodiments, the gas exchanger may be configured to manipulate the concentration of the sweep gas that is exposed to the patient's blood to transfer oxygen and to remove the carbon dioxide, such as by using sweep gases that include oxygen, blended oxygen and atmospheric air, other medical gases, and the like.

The present invention includes a compact dual chamber gas exchanger having a low priming volume, small gas exchange surface area, and the ability to disrupt boundary layer effect. The dual chamber gas exchanger also removes carbon dioxide while providing oxygen transfer. The dual chamber gas exchanger includes an outer housing that encloses the internal components and hosts connectors, a blood inlet, and an annular outer fiber bundle of hollow fiber membranes. The dual chamber gas exchanger is configured for a wide range of uses, such as cardiopulmonary bypass, extracorporeal membrane oxygenation (ECMO), as an integrated pump-oxygenator, passive respiratory support device (e.g., configuration for right ventricle to pulmonary artery or configuration for pulmonary artery to left atrium), ambulatory cardiopulmonary, and respiratory support, or the like.

The outer fiber bundle is centrally located in the housing and further includes fibers, upper potting, and lower potting. The upper potting and lower potting hold the fibers within the housing. In one embodiment, the outer fiber bundle includes a blood distributor configured as a spiral volute wrapping around the inner surface of the housing. The blood distributor is coupled to the blood inlet near the upper potting or lower potting. The blood distributor is configured to discharge blood around the outer fiber bundle such that it creates a pressurized annular blood volume surrounding the outer fiber bundle, and such that blood flows axially through the gas exchange membranes of the outer fiber bundle.

In an alternative embodiment, the blood distributor of the dual chamber gas exchanger includes a rectangular inlet or first gate opening at one side of the outer housing from one end to the other end of the potting areas. The rectangular gate opening is typically a vertically oriented slot configured to couple the blood inlet to discharge the incoming blood to the outer fiber bundle. Thus, the blood generally flows circumferentially through the gas exchange membranes of the outer fiber bundle, usually exiting at a second or outlet gate as described hereinbelow.

One embodiment of the dual chamber gas exchanger further includes an annular inner fiber bundle of hollow fiber membranes. The annular inner fiber bundle is concentrically located within the outer fiber bundle, and further includes fibers, an upper potting, and a lower potting. The upper potting and lower potting of the annular inner fiber bundle hold the fibers in place in the housing.

Another embodiment of the dual chamber gas exchanger further includes an intermediate housing, typically formed as a cylindrical wall, that is configured to substantially separate the outer fiber bundle and inner fiber bundle. Thus, the intermediate housing is generally located between a radially inward surface of the outer fiber bundle and a radially outward surface of the inner fiber bundle. An intermediate annular space is formed between a radially inward surface of the intermediate housing and the radially outward surface of the inner fiber bundle which provides an annular flow path around the inner fiber bundle to allow a radially inward blood flow path through the inner fiber bundle. In other embodiments, the intermediate housing may be configured to provide circumferential or axial flow through the inner fiber bundle.

The dual chamber gas exchanger further includes a thin slot at the upper potting area, which allows the blood to exit the outer fiber bundle and enter the intermediate annular space existing between the intermediate housing wall and the outer annular surface of the inner fiber bundle. In another embodiment having a circumferential flow path through the outer fiber bundle, the dual chamber gas exchanger includes a rectangular gate that is configured to allow blood flow to flow from the outer fiber bundle into the intermediate annular space.

The dual chamber gas exchanger includes components for transferring fluids, including a blood inlet, a blood outlet, and at least one gas inlet. The blood outlet is configured to collect the oxygenated blood from the fibers and further couples to a cannula through which the oxygenated blood is returned to the patient. The blood outlet is generally located at a central location at a top portion of the housing and is fluidly coupled to the inner fiber bundle, such as to the upper potting of the inner fiber bundle.

The at least one gas inlet, such as two gas inlets of one embodiment, are configured to provide separate gas passages for gases, such as oxygen and/or air, to enter the hollow fibers. The at least one gas inlet is positioned on a bottom portion of the housing. In one embodiment, the at least one gas inlet forms two separate gas chambers with the lower potting of the two bundles of hollow fiber membranes.

The two gas outlets are configured to provide gas passages for gases, such as the oxygen and/or air to leave the hollow fibers. The gas outlets are generally located on the top portion of the housing and generally form two separate gas chambers with the upper potting of the two bundles of hollow fiber membranes.

In another embodiment, the blood gas exchanger includes a blood sample port or a blood gas sensor that is configured to allow external sampling of the blood within the blood gas exchanger. For example, the blood sample port may be fluidly coupled to the blood inlet or blood outlet. The blood sample port may further include an oxygen saturation detector affixed to the blood outlet, and a temperature port affixed to the blood outlet.

While there may be different considerations and requirements for each clinical scenario, a blood exchanger that is efficient, long-term biocompatible, long-term durable and versatile is universally desirable. In other words, it is desirable to use minimal necessary fiber membranes to achieve the most efficient gas transfer while minimizing blood trauma and maintaining long-term durability and reliability. It is also flexible to accommodate various sweep gas sources to provide oxygen transfer, carbon dioxide removal, or both, for various clinical applications.

In a first aspect, the present invention provides a blood oxygenator comprising a housing which includes a blood inlet, a blood outlet, a stripping gas inlet, an oxygenation gas inlet, and at least one gas outlet. An oxygenator fiber bundle is disposed within the housing and is configured so that blood flows through a blood flow region in the oxygenator fiber bundle in a predetermined path from the blood inlet to the blood outlet. The stripping gas inlet is configured to direct a flow of stripping gas through a stripping region of the oxygenator fiber bundle to the at least one gas outlet. The oxygenation gas inlet is configured to direct a flow of oxygenation gas through an oxygenation region of the oxygenator fiber bundle to the at least one gas outlet. The stripping gas region of the oxygenator fiber bundle is upstream of the oxygenation region of the oxygenator fiber bundle. The term "upstream" refers to the direction of blood flow so that the blood to be oxygenated is first exposed to the stripping gas in the stripping region and thereafter exposed to the oxygenation gas in the oxygenation region of the fiber bundle.

In a first set of exemplary embodiments, the blood oxygenators of the present invention may have a cylindrical fiber bundle where at least a portion of the blood flow path is in a radially inward or radially outward direction. In such embodiments, a portion of the fiber bundle along a central axis will typically be open to provide an outlet or inlet plenum to receive blood from or distribute blood to the cylindrical fiber bundle, respectively. In still other embodiments, the fiber bundle is cylindrical and at least a portion of the blood flow path follows an annular path, where the bundle will typically have a blood inlet or outlet plenum along the central axis of the fiber bundle. In still other embodiments, at least a portion of the blood flow path may be unidirectional across the oxygenator fiber bundle.

In certain specific examples, the fiber bundle of the oxygenator is cylindrical, having an outer portion of the blood flow path which follows an annular path and an inner portion of the blood flow path which follows a radially inward path. In these examples, the blood inlet typically feeds the outer portion of the fiber bundle, and the inner portion of the fiber bundle feeds the blood outlet. More specifically, the stripping region may be disposed at least in part in the outer portion of the blood flow path and the oxygenation region may be disposed at least in part in the inner portion of the blood flow path where the blood inlet feeds the inner portion and the outer portion feeds the blood outlet. Alternatively, the stripping region may be disposed at least in part in the inner portion of the blood flow path and the oxygenation region is disposed at least in part in the outer portion of the blood flow path.

The blood oxygenator may further comprise a cylindrical wall separating the outer portion and the inner portion of the cylindrical fiber bundle, where blood flows from the blood inlet through an axial opening in the housing into the outer portion of the fiber bundle and flows annularly through the outer portion of the fiber bundle to thereafter through an axial opening in the cylindrical wall and into a distribution ring surrounding the inner bundle from where the blood flows radially inwardly through the inner portion of the fiber bundle to an axial collection region along a center axis of the inner portion of the fiber bundle.

In other embodiments, the oxygenation fiber bundles of the blood oxygenator of the present invention may have a cross-sectional area where the stripping region that receives the stripping gas from the stripping gas inlet has an inlet area that comprises from 20% to 80% of said cross-sectional area and the oxygenation region that receives the oxygenation gas from the oxygenation gas inlet has an inlet area that comprises from 80% to 20% of said cross-sectional area.

In still further embodiments, the blood oxygenators may further comprise a manifold divider which divides and directs both (1) the stripping gas from the stripping gas inlet to the stripping region of the oxygenator fiber bundle and (2) the oxygenation gas from the oxygenation gas inlet to the oxygenation region of the oxygenator fiber bundle. The manifold divider may be disposed in a manifold which receives the stripping gas from the stripping gas inlet and the oxygenation gas from the oxygenation gas inlet, where the manifold is typically open to an entire gas inlet side of the oxygenation fiber bundle and placement of the manifold divider controls an inlet area of the stripping region that receives the stripping gas from the stripping gas inlet and an inlet area of the oxygenation region that receives the oxygenation gas from the oxygenation gas inlet. The manifold divider may be fixed or may be moveable, the latter case allowing the relative areas of the stripping and oxygenation regions in the fiber bundle to be adjusted during use or between uses.

In yet further embodiments, the oxygenation fiber bundles of the blood oxygenators may comprise an upper potting and a lower potting. The manifold may be located within the housing adjacent to one of the pottings, and a blood pump may be connected to said blood inlet. An oxygenation gas source may be connected to the oxygenation gas inlet and a stripping gas source may be connected to the stripping gas inlet.

In a second aspect, the present invention provides methods for oxygenating blood. A blood oxygenator having a (1) housing with a blood inlet, a blood outlet, a stripping gas inlet, an oxygenation gas inlet, and at least one gas outlet and (2) an oxygenator fiber bundle disposed within the housing is provided. Blood is flowed through the blood inlet, through the oxygenator fiber bundle, and out the blood outlet. A stripping gas is flowed through the stripping gas inlet, and an oxygenation gas is flowed through the oxygenation gas inlet. The stripping gas flows through a stripping region of the oxygenator fiber bundle to the at least one gas outlet, and the oxygenation gas flows through an oxygenation region of the oxygenator fiber bundle to the at least one gas outlet. The stripping gas region of the oxygenator fiber bundle is disposed upstream of the oxygenation region of the oxygenator fiber bundle. The arrangement achieves a particularly efficient $CO_2$ removal and oxygen incorporation and, in particular, can reduce the need for pure oxygen to perform both the $CO_2$ stripping and the blood oxygenation.

In particular embodiments of the methods of the present invention, the blood may travel through the stripping region of the oxygenator fiber bundle in an annular flow path, and in other embodiments, the blood travels through the oxygenation region of the oxygenator fiber bundle in a radially inward flow path. In still other embodiments, the blood may travel through the stripping region and the oxygenation region of the oxygenator fiber bundle in a straight direction. In some instances, the blood may travel through the oxygenator fiber bundle in a substantially uniform blood flow distribution. In other instances, the fiber bundle may have a cross-sectional area where the stripping region that receives the stripping gas from the stripping gas inlet has an inlet area that comprises from 20% to 80% of the cross-sectional area and the oxygenation region that receives the oxygenation gas from the oxygenation gas inlet has an inlet area that comprises from 80% to 20% of the cross-sectional area. The methods of the present invention may further comprise moving a manifold divider which directs the flow stripping gas from the stripping gas inlet to the stripping region of the oxygenator fiber bundle, as well as the oxygenation gas from the oxygenation gas inlet to the oxygenation region of the oxygenator fiber bundle, in order to adjust relative areas of the stripping region and the oxygenation region of the oxygenation fiber bundle.

DETAILED DESCRIPTION OF THE INVENTION

Figure 1:
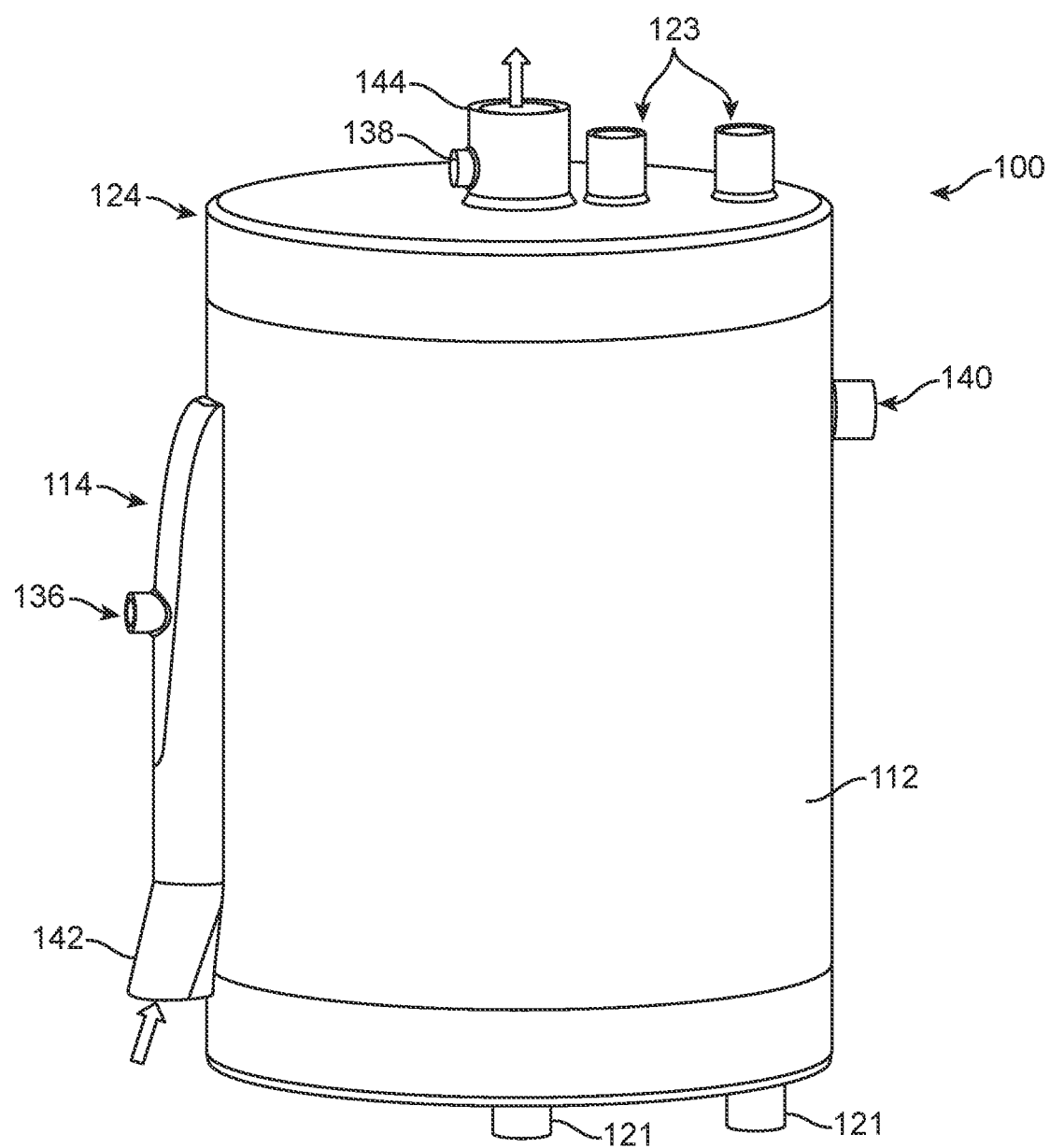
FIG. 1: Perspective view of a first embodiment of a dual chamber gas exchanger with a circumferential-radial flow path, according to the principles of the present invention.

Referring to FIGS. 1-22, a dual chamber gas exchanger 100 is configured to use two separate sweep gases (e.g., ventilating gases) to allow the dual chamber gas exchanger 100 to be used in various clinical applications. For example, the dual chamber gas exchanger 100 uses separate flow paths in separate chambers of a dual gas flow chamber 124, such as a first chamber 110 and a second chamber 113, for transferring oxygen to the blood and removing carbon dioxide from the blood. The dual chamber gas exchanger 100 of the current embodiment includes an outer housing 112, a blood distributor 114, an outer fiber bundle 116 of hollow membranes, an intermediate housing 118, an inner fiber bundle 120 of hollow membranes, an inner flow deflector 122, and the dual gas flow chamber 124. The dual chamber gas exchanger 100 can be used in various clinical scenarios; for example, cardiopulmonary bypass during cardiothoracic surgeries, extracorporeal membrane oxygenation (ECMO) for cardiopulmonary support or respiratory support in hospitals, ambulatory respiratory support (see FIG. 13) out of intensive care unit, at a patient's home, and the like.

The outer housing 112 and the intermediate housing 118 are configured to enclose the outer fiber bundle 116 to form various blood flow paths in the outer fiber bundle 116 and the inner fiber bundle 120 (see FIGS. 2, 3, 4, 6, 7, 8A, 8B, 14, 15, 16, 17, 18, 19, 20, 21, and 22). For example, each of the blood flow paths may be at least one of axial, circumferential, or radial flow paths, etc. The inner flow deflector 122 is configured to deflect or guide blood flow from the inner fiber bundle 120 towards a blood outlet 144. The inner flow deflector 122 (see FIGS. 2, 3, 4, 6, 7, 8B, 14, 15, 17, 18, 20, and 21) of the current embodiments has a general shape of a cylinder with a conical-like top and is substantially concentrically located in the center of the inner fiber bundle 120.

The dual gas flow chamber 124 receives sweep gas and distributes the sweep gas into the fiber membranes in both the inner fiber bundle 120 and the outer fiber bundle 116 (FIGS. 2, 6, 14, 15, 17, 18, 20, 21, and 23). The sweep gas of the current embodiments includes air, oxygen, a mixture of oxygen and air, or another ventilating gas. The intermediate housing 118 is configured to allow blood to flow (e.g., in a substantially radial, axial, and/or circumferential direction) through the inner fiber bundle 120, and to enclose the inner fiber bundle 120. The inner fiber bundle 120 and outer fiber bundle 116 include gas-exchange membrane fibers, such as hollow membrane fibers, configured to transfer oxygen to the blood and remove carbon dioxide from the blood that flows across the membrane fibers. The inner fiber bundle 120 and the outer fiber bundle 116 can be annular fiber bundles (see FIGS. 2, 6, 14, 17, 20, and 23A and 23B) or square forms (see FIG. 24) consisting of a plurality (e.g., thousands) of gas permeable hollow membrane fibers or membrane fibers. The inner fiber bundle 120 and the outer fiber bundle 116 are generally centrally and concentrically located within the outer housing 112, with the intermediate housing 118 separating the inner fiber bundle 120 and the outer fiber bundle 116, as discussed above.

The hollow fiber membranes of the outer fiber bundle 116 and the inner fiber bundle 120 are coupled to an upper potting 117 and a lower potting 119 that are configured to fluidly communicate sweep gases into and from the hollow fiber membranes (e.g., into the hollow fiber membranes from a gas inlet 121 and/or from the hollow fiber membranes to a gas outlet 123, such as gas outlet 1 and gas outlet 2). Thus, the upper potting 117 is positioned at an upper portion within the outer housing 112 and a lower potting 119 is positioned at a bottom portion within the outer housing 112. Furthermore, each of the inner fiber bundle 120 and the outer fiber bundle 116 are configured to be sealed from each other, including at the upper potting 117 and the lower potting 119, to prevent undesired flow paths of the blood and/or sweep gases.

In one example, the sweep gas may be selected based on the clinical application, such as by using oxygen or an oxygen-rich gas to substantially transfer oxygen to blood in the outer fiber bundle 116 and to substantially remove carbon dioxide in the inner fiber bundle 120. Alternatively, air (e.g., atmospheric air) or a combination of air and oxygen may be used. The flow of sweep gas is separated into flow paths (e.g., for transferring oxygen and for removing carbon dioxide) to control the flow rate of each sweep gas and/or content independently from the other sweep gas.

Referring to FIGS. 1, 2, 5, 6, 14, 15, 17, 18, 20, 21 and 23, the dual chamber gas exchanger 100 is further configured to control how many of the hollow membrane fibers are in contact with the sweep gas. For example, one flow path can be controlled to independently deliver oxygen and/or air from another flow path. Thus, the dual chamber gas exchanger 100 increases flexibility using various gas sources for oxygen transfer and carbon dioxide removal. For example, depending on clinical applications, both of the inner fiber bundle 120 and outer fiber bundle 116 can be used for oxygen transfer and/or carbon dioxide removal, or only the outer fiber bundle 116 is used for oxygen transfer while the inner fiber bundle 120 is used to remove carbon dioxide and vice versa.

Furthermore, the dual chamber gas exchanger 100 can be configured to increase the flow rate of one gas (e.g., oxygen or air). For example, a sweep gas from one flow path can be recirculated such that it is combined with the gas in the other flow path for a clinical application in which increasing oxygen may have a greater clinical need than carbon dioxide removal. As a further example, the clinician can increase the sweep gas flow rate and/or surface area of the oxygenator membrane (further described below) that is exposed to air if increased carbon dioxide removal is required.

Referring to FIGS. 2, 3, 6, 7, 14, 15, 17, 18, 20, 21, and 23, the first chamber 110 of the dual chamber gas exchanger 100 can be configured to transfer the sweep gas (e.g., oxygen) to the blood or remove the carbon dioxide from the blood. For example, the flow rate of the sweep gas for transferring oxygen may be approximately between 1 liters per minute and 6 liters per minute. An oxygen source then provides the sweep gas to the first chamber 110. In one embodiment, the oxygen source is a small capacity, light weight, battery operated, portable oxygen concentrator (e.g., a commercially-available oxygen concentrator).

Figure 11:
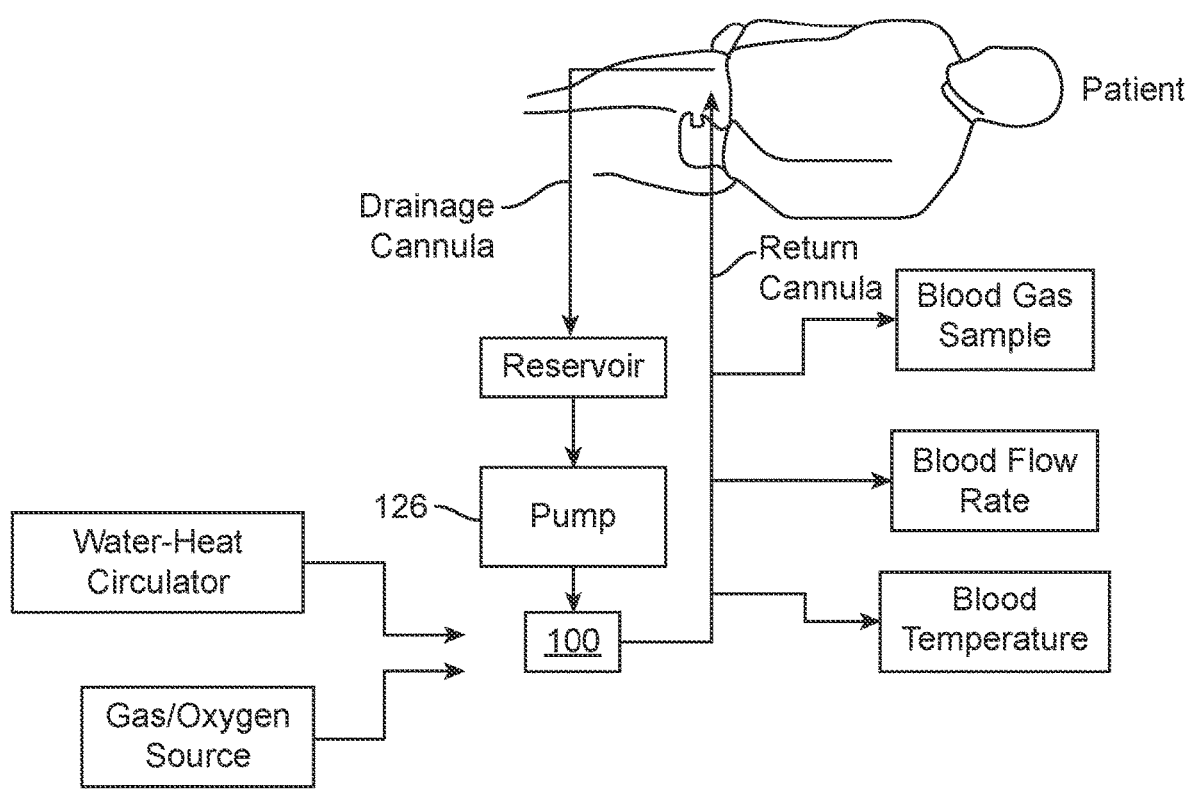
FIG. 11: Schematic of the dual chamber blood oxygenator showing various components used for a cardiopulmonary bypass surgery application.
Figure 12:
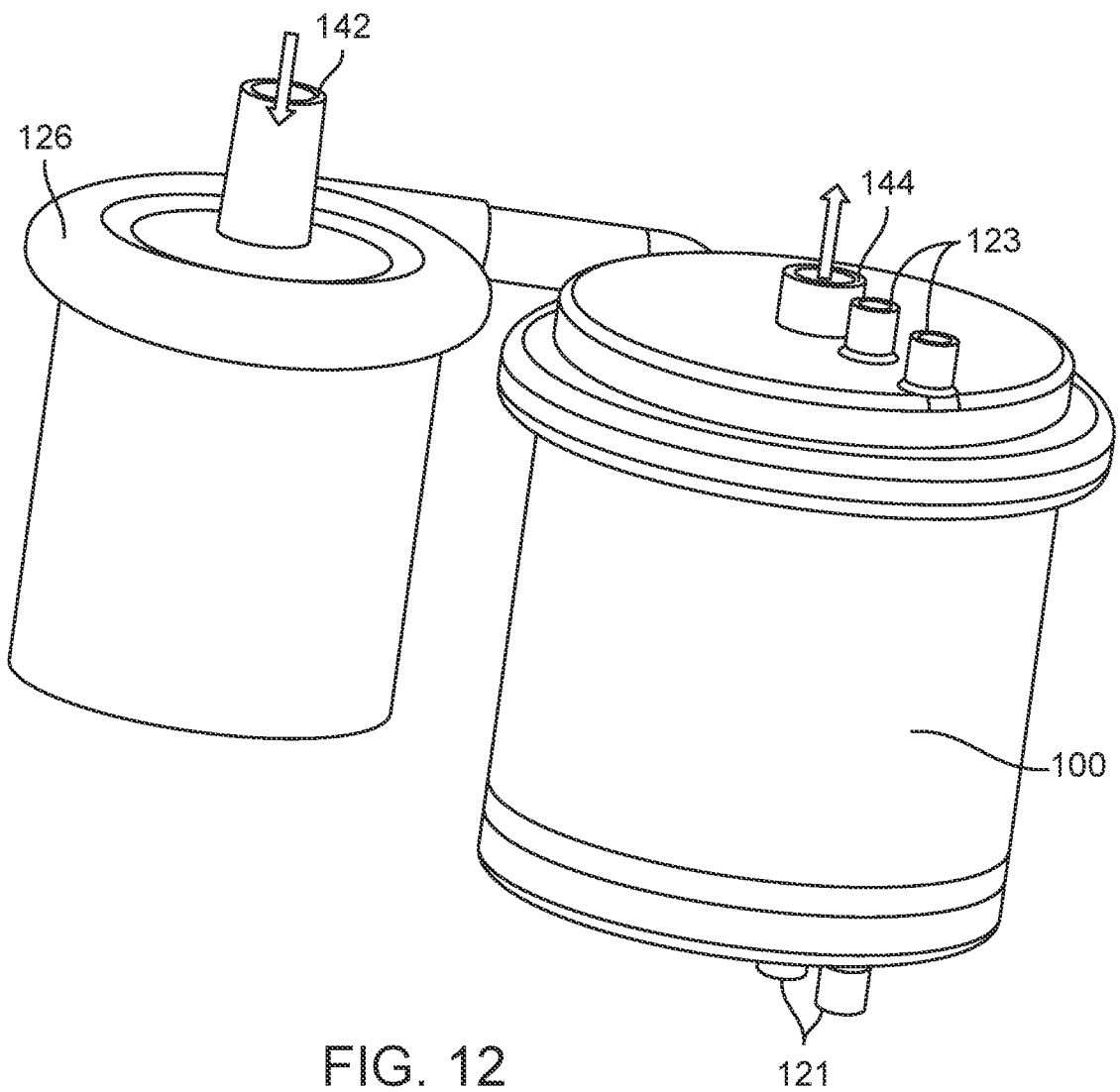
FIG. 12: Illustration of a dual chamber gas exchanger for use as a detachable integrated pump-oxygenator (e.g., integrated pump-oxygenator), according to another embodiment of the present invention.
Figure 13A:
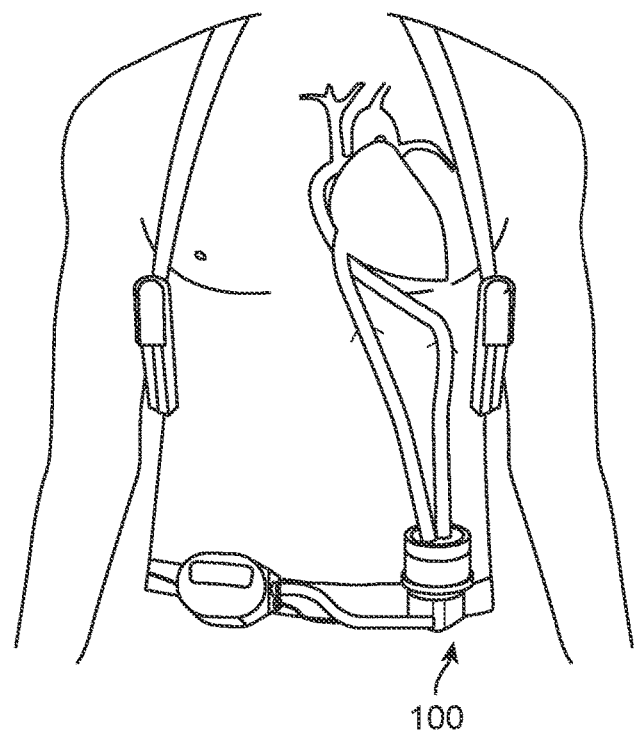
FIGS. 13A and 13B: Illustrations of a dual chamber gas exchanger for use as an ambulatory respiratory and/or cardiopulmonary support, according to another embodiment of the present invention ((a) harness-like configuration; (b) wheeled configuration).
Figure 13B:
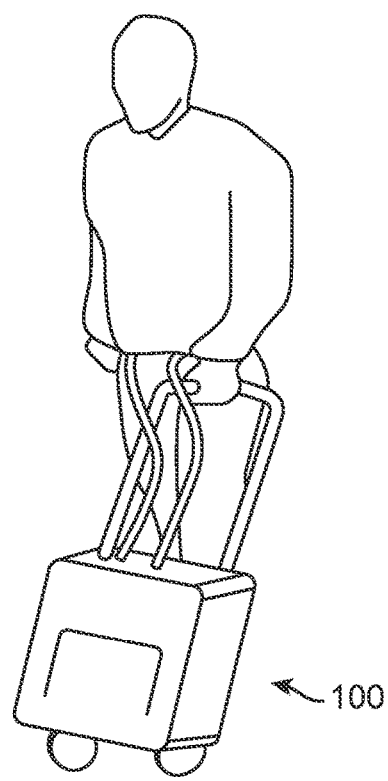
Figure 14:
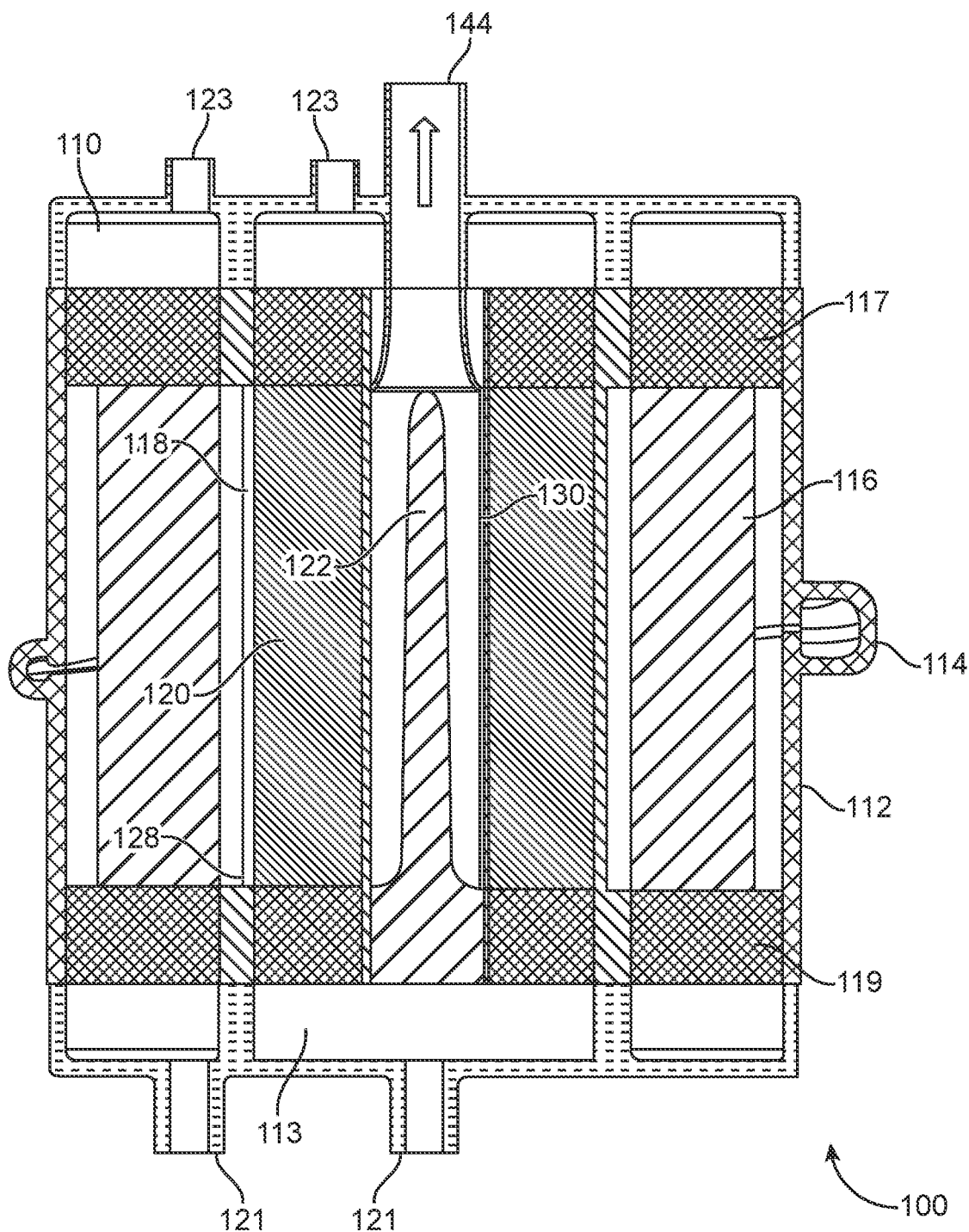
FIG. 14: Vertical cross-sectional view of a dual chamber gas exchanger with a radial flow path design in an outer fiber bundle and a circumferential flow path in an inner fiber bundle, according to another embodiment of the present invention.
Figure 15:
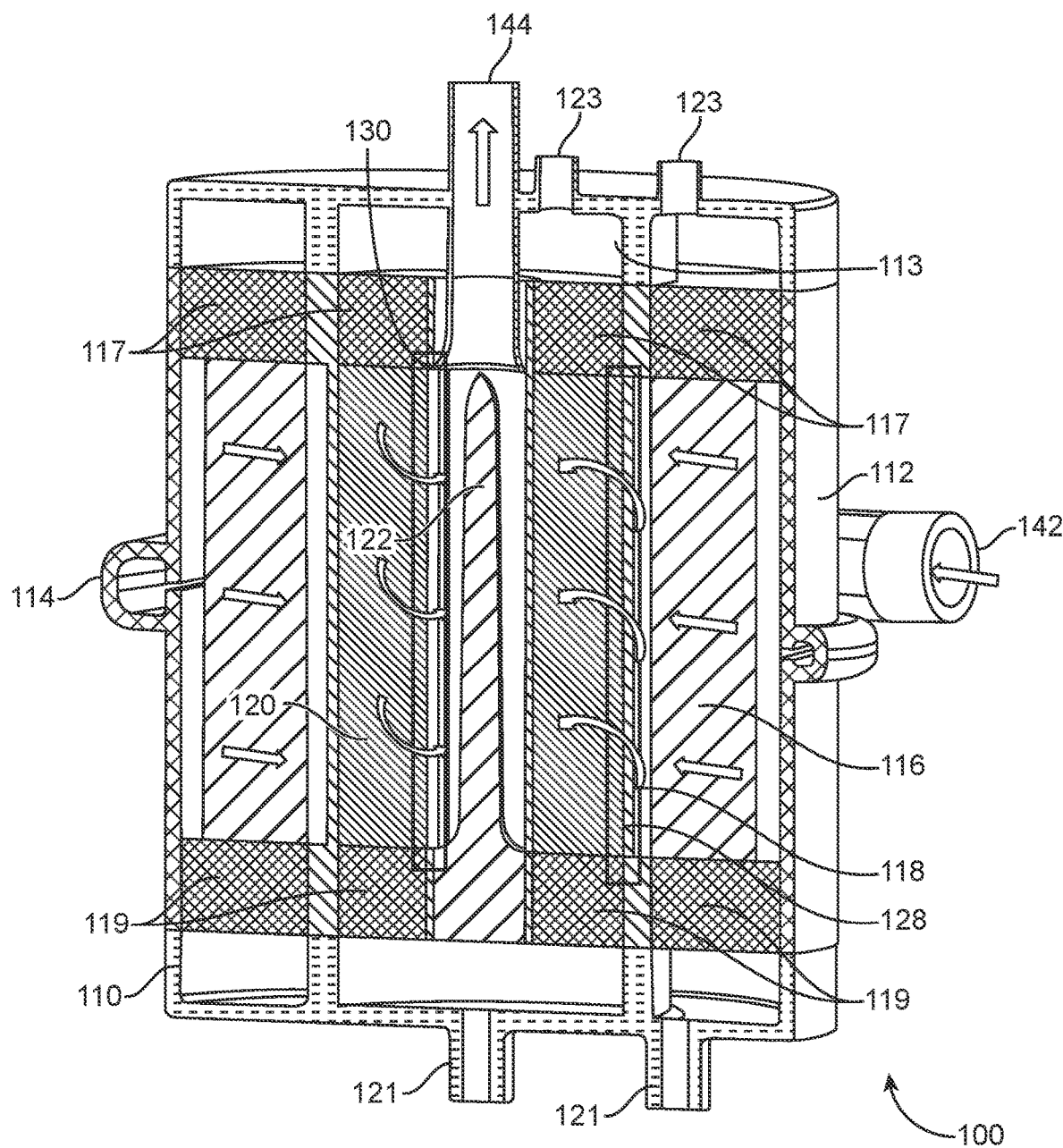
FIG. 15: Vertical cross-sectional view of the dual chamber gas exchanger of the embodiment of FIG. 14 with arrows showing blood flow directions.
Figure 16:
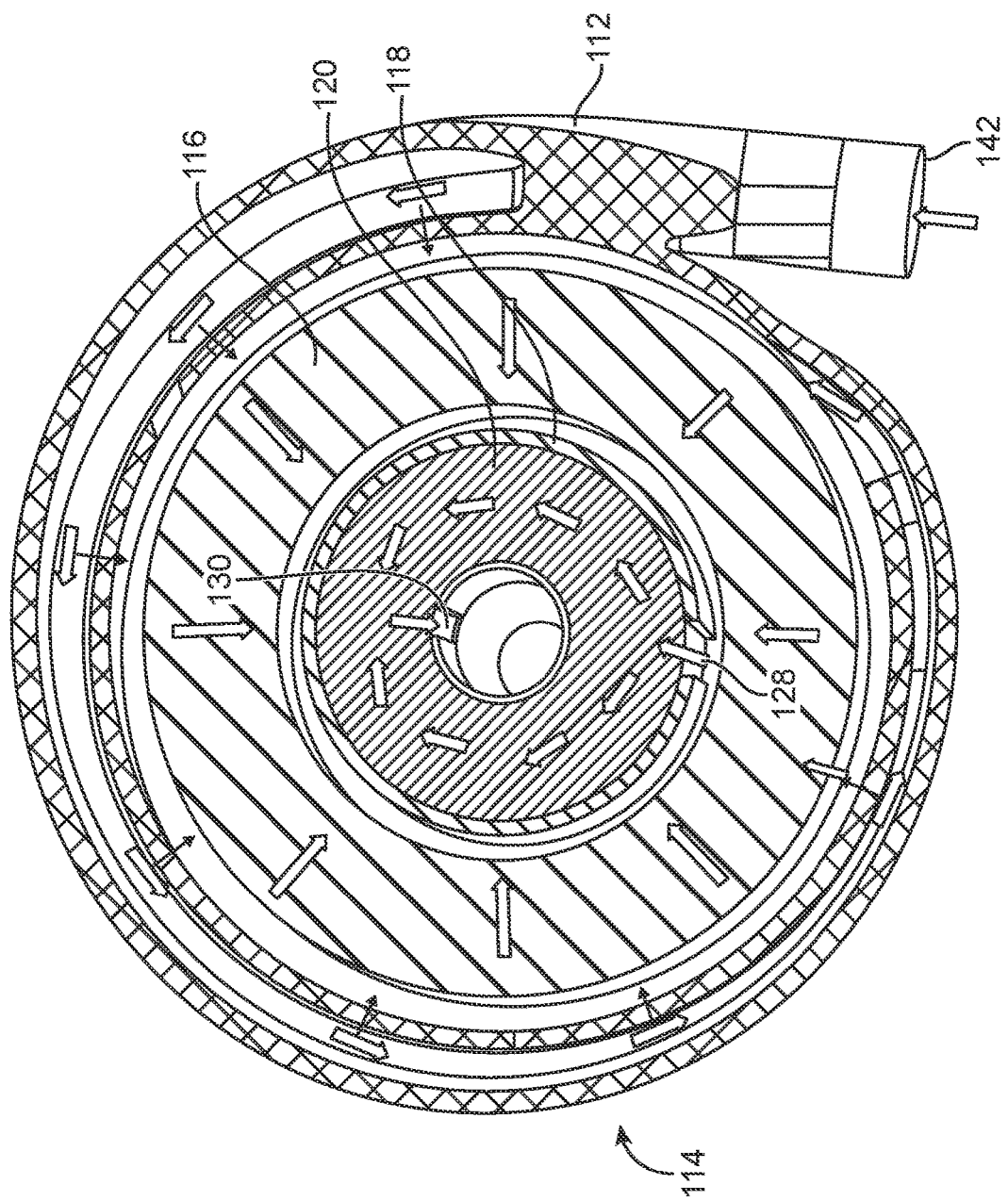
FIG. 16: Horizontal cross-sectional view of the blood flow paths in a spiral volute, the outer fiber bundle and the inner fiber bundle of the dual chamber gas exchanger similar to those of FIG. 14.
Figure 17:
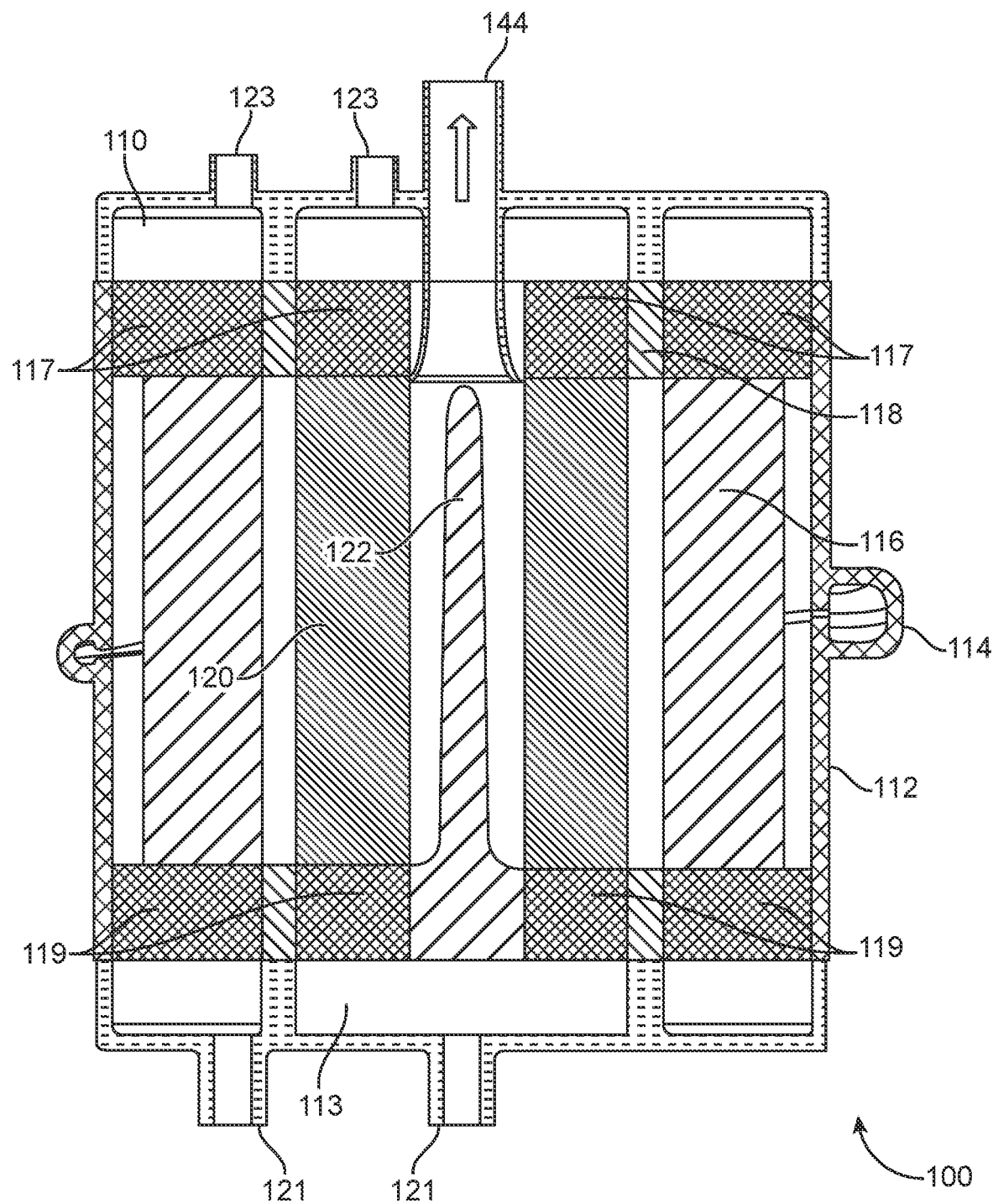
FIG. 17: Schematic, vertical cross-sectional view of a dual chamber gas exchanger having a radial blood flow through inner and outer annular chambers.
Figure 18:
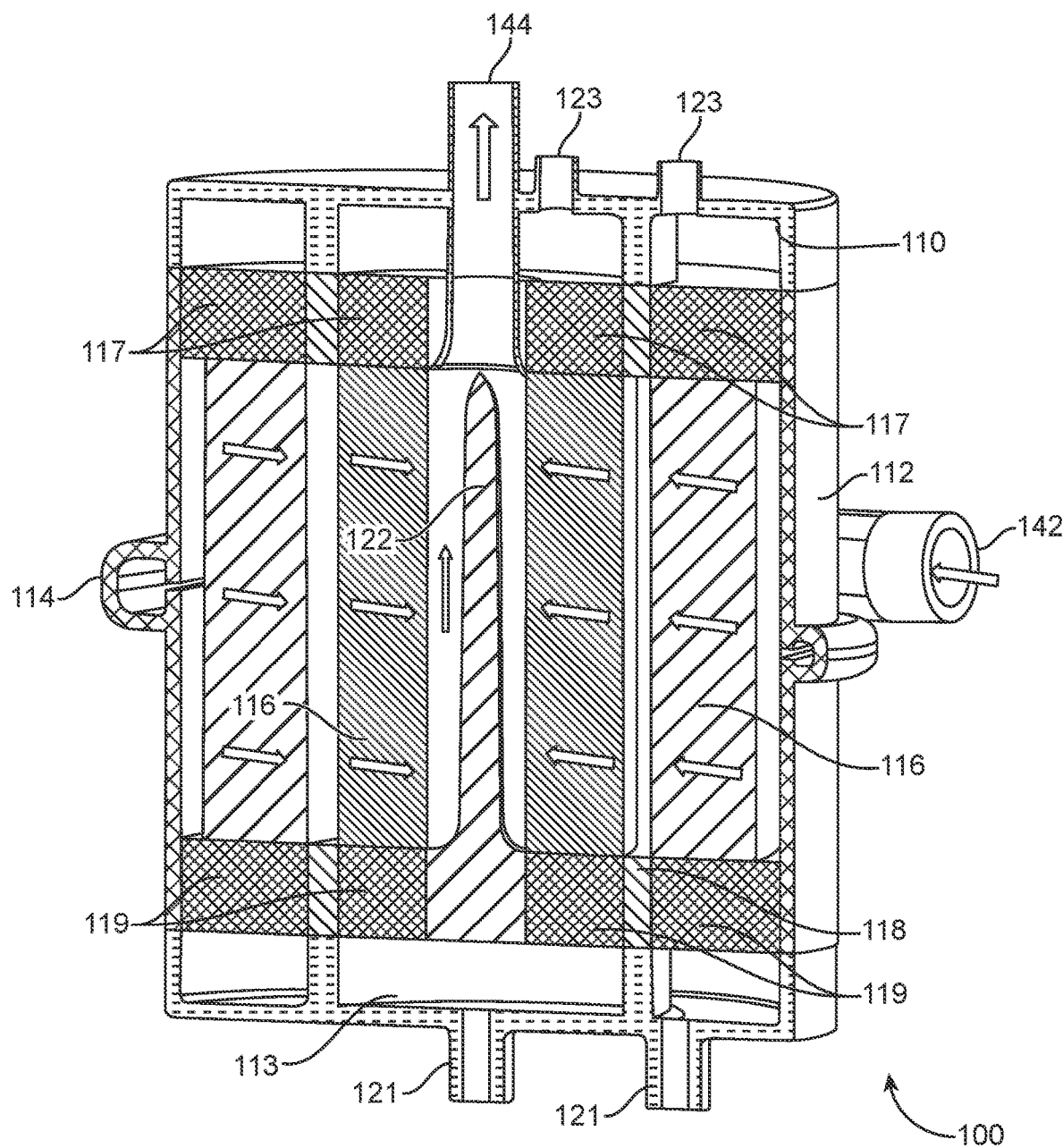
FIG. 18: Vertical cross-sectional view of the dual chamber gas exchanger of the embodiment of FIG. 17 with arrows illustrating radial blood flow paths in the inner fiber bundle and outer fiber bundles.
Figure 19:
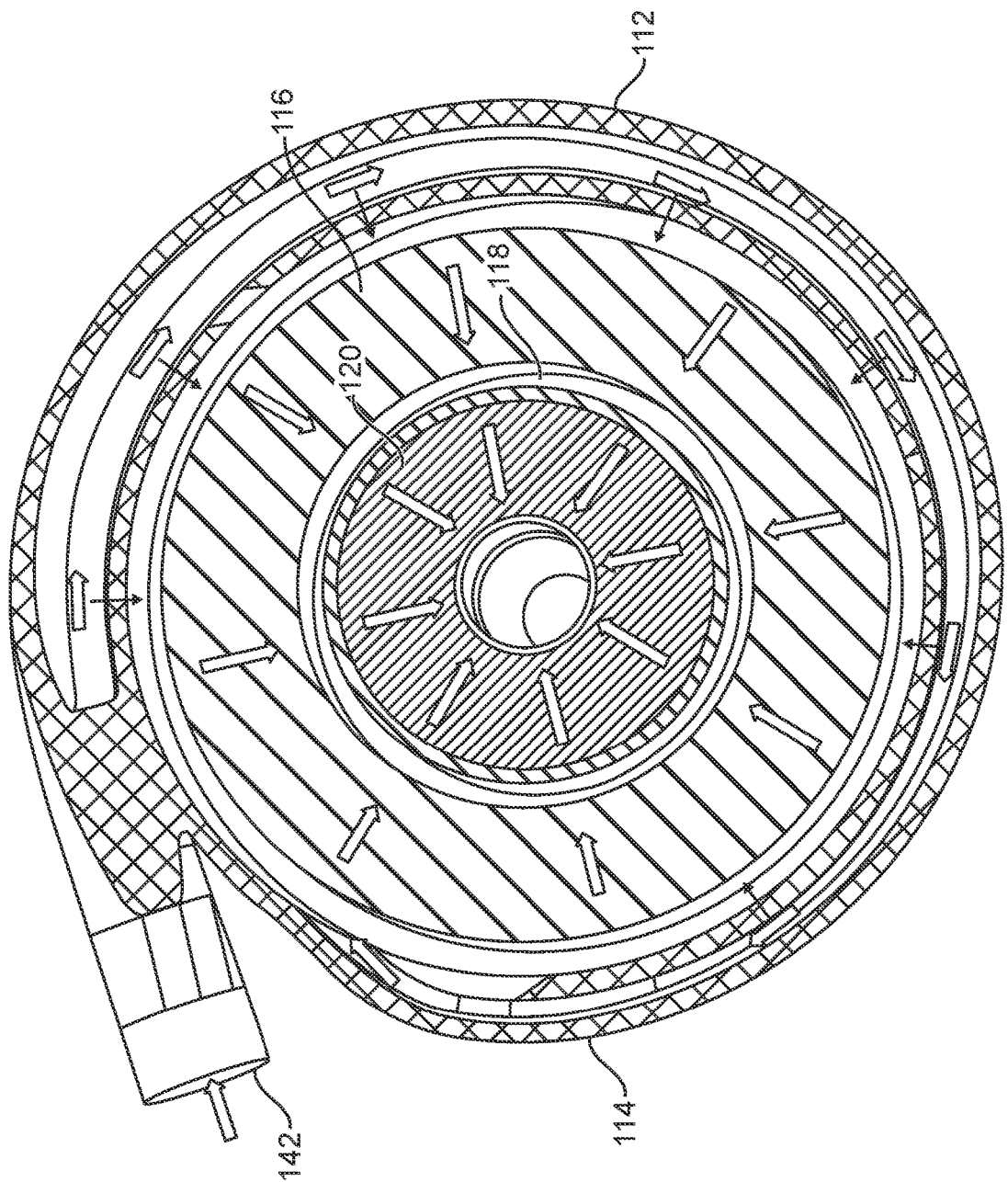
FIG. 19: Horizontal cross-sectional view of a spiral volute, the outer fiber bundle, and the inner fiber bundle of the dual chamber gas exchanger illustrating blood flow paths similar to the embodiment of FIG. 17.
Figure 20:
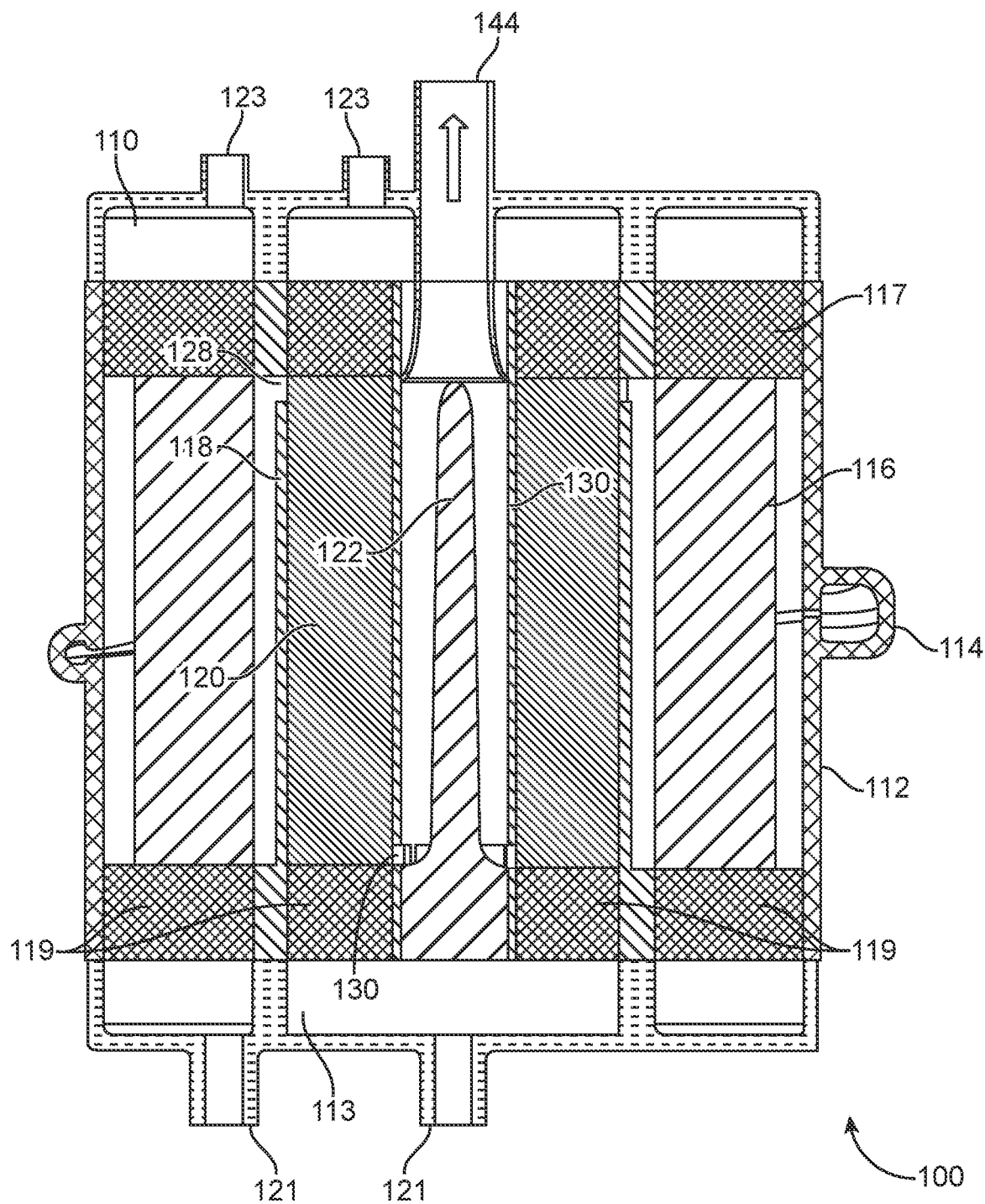
FIG. 20: Vertical cross-sectional view of a dual chamber gas exchanger having a radial flow path in an outer fiber bundle and an axial flow path in an inner fiber bundle, according to another embodiment of the present invention.
Figure 21:
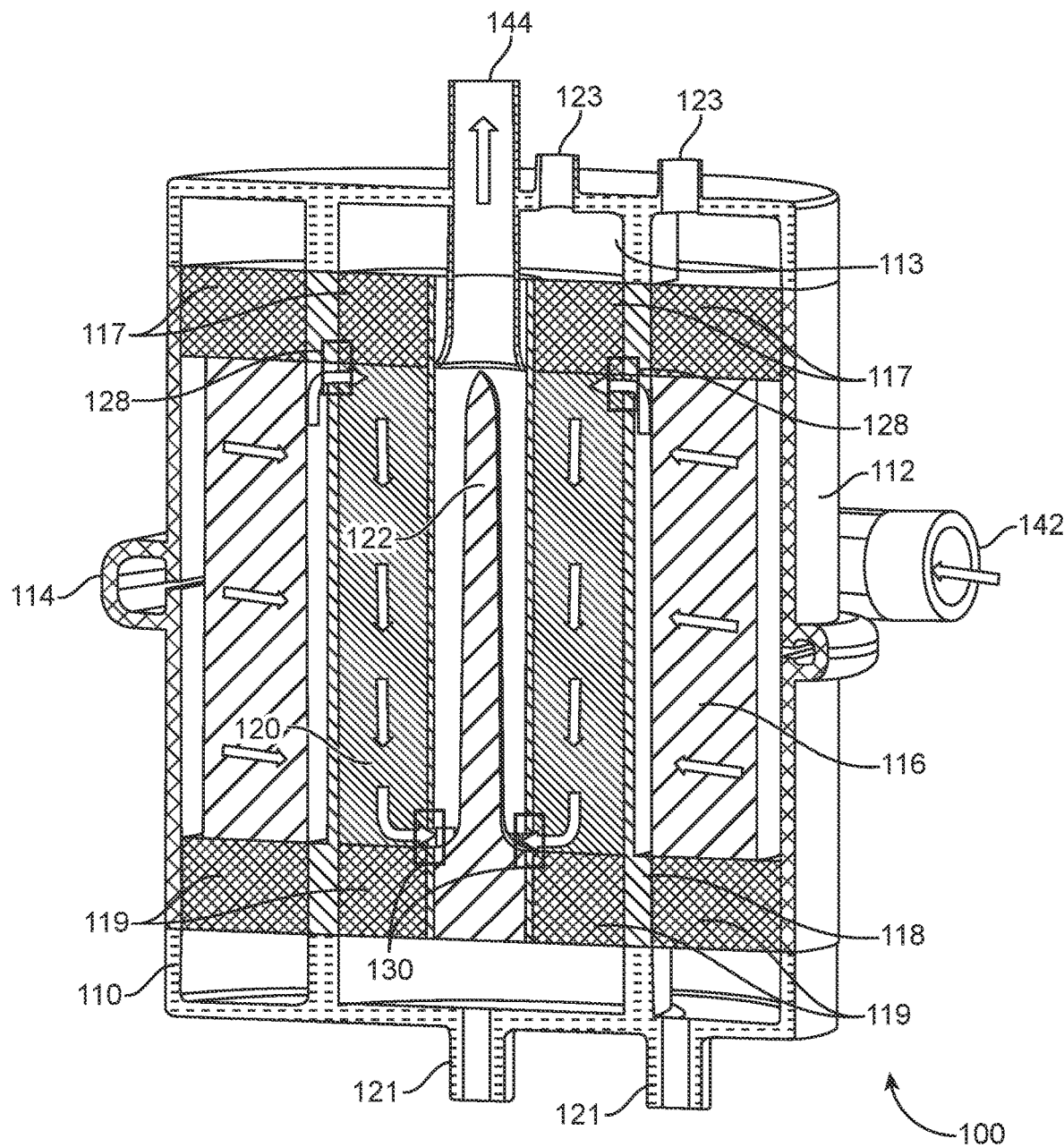
FIG. 21: Vertical cross-sectional view of the dual chamber gas exchanger of FIG. 20 with arrows illustrating a radial blood flow path in the outer fiber bundle, an axial blood flow path in the inner fiber bundle, two gas inlets, and two gas outlets.
Figure 22:
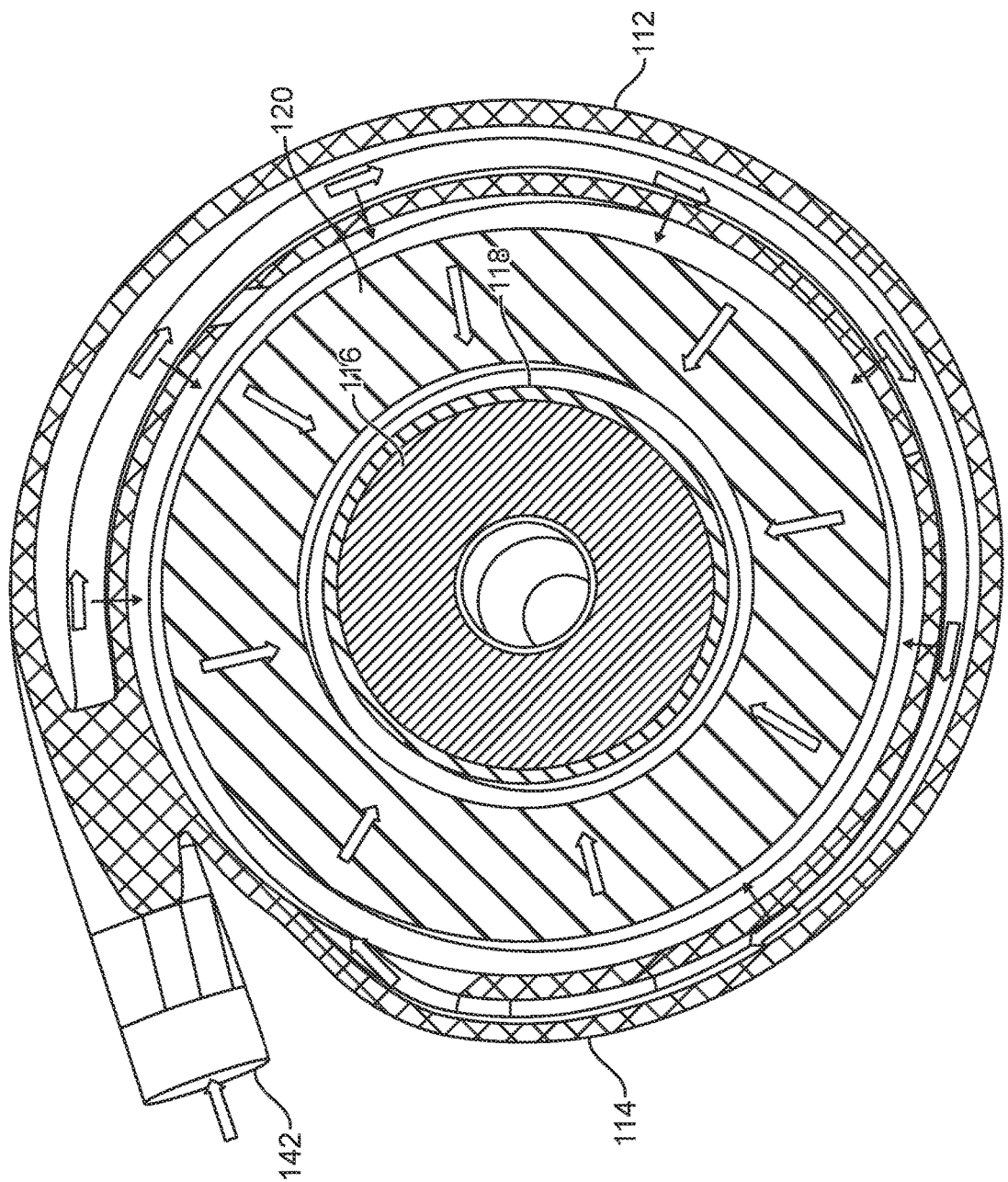
FIG. 22: Horizontal cross-sectional view of a spiral volute blood inlet in a dual chamber gas exchanger similar to that of FIG. 20 with arrows illustrating blood flow paths in the spiral volute and the outer fiber bundle.

The oxygen concentrator converts air into high oxygen concentration (e.g., approximately >90% oxygen concentration) gas. The oxygen concentrator can be integrated into a portable drive console that is configured to enclose the oxygen concentrator and other components, such as a power source (such as a battery), blood pump controls, flow sensors, and blood gas sensors (FIGS. 11 and 13). For example, one embodiment can include a detachable pump 126 to form an integrated pump-oxygenator (e.g., integrated pump-oxygenator; see FIG. 12) that includes a typical blood pump 126 and pump driver that are controlled by the blood pump controls. The blood pump 126 can be simply coupled and uncoupled from the dual chamber gas exchanger 100 by using a quick connector, typical fastener, or the like. However, in other embodiments, the oxygen source may be a fixed or portable oxygen tank, atmospheric air, or the like.

Again referring to FIGS. 2, 3, 6, 7, 14, 15, 17, 18, 20, 21, and 23, the second chamber 113 of the dual chamber gas exchanger 100 can be configured to remove carbon dioxide from the blood or transfer oxygen to the blood. For example, the flow rate of the sweep gas for removing carbon dioxide may be approximately 6 liters per minute to 18 liters per minute. In one embodiment, a small air fan compresses and mixes air with the sweep gas (e.g., oxygen or oxygen-rich gas) from the first chamber 110 to generate a high sweep gas flow for carbon dioxide removal. The enclosed dual gas flow chamber 124 of the current embodiment is positioned below the lower potting 119 or above the upper potting 117 of the inner fiber bundle 120 and the outer fiber bundle 116.

Still referring to FIGS. 2, 3, 6, 7, 14, 15, 17, 18, 20, 21, and 23, the dual gas flow chamber 124 includes the first chamber 110 and the second chamber 113 that are each configured to receive one of the sweep gases from the two gas inlets 121 (e.g., gas inlet 1 and gas inlet 2). For example, the sweep gases in each first chamber 110 and outer chamber 113 may have different compositions and/or flow rates. The gas inlets 121 distribute the sweep gases to the open lumen fibers that are imbedded in the upper potting 117 and the lower potting 119 of the inner fiber bundle 120 and outer fiber bundle 116, respectively. In the current embodiments, oxygen or oxygen-rich gas flows through open fiber lumens in the upper potting 119 and diffuses across an outer wall of individual hollow fiber membranes in the first chamber 110 into the blood where blood oxygenation takes place. Furthermore, carbon dioxide from the blood diffuses into the lumens of the hollow fiber membranes and is removed from the blood. The sweep gas flows through the hollow fiber membranes and exits the dual gas flow chamber 124 through the lower potting 119. In the current embodiments, the sweep gases exit the dual chamber gas exchanger 100 by venting into the atmosphere. Thus, the dual chamber gas exchanger 100 receives and diffuses the sweep gases into separate fiber membrane bundles for blood oxygenation and carbon dioxide removal.

Figure 2:
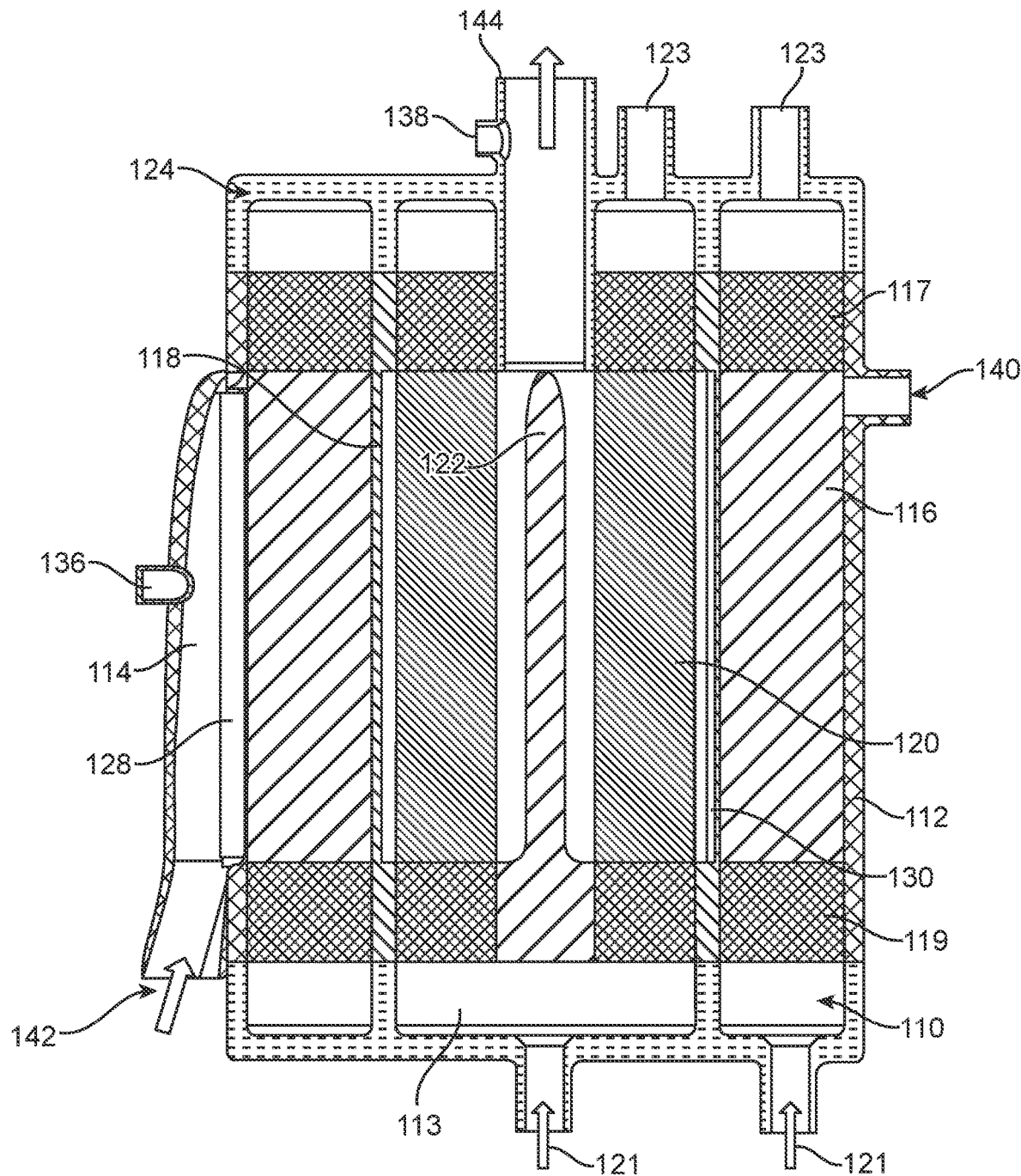
FIG. 2: Vertical cross-sectional view of the dual chamber gas exchanger of FIG. 1 having a circumferential flow path design in an outer fiber bundle and a radial flow path in an inner fiber bundle, two gas inlets, and two gas exhausts.
Figure 3:
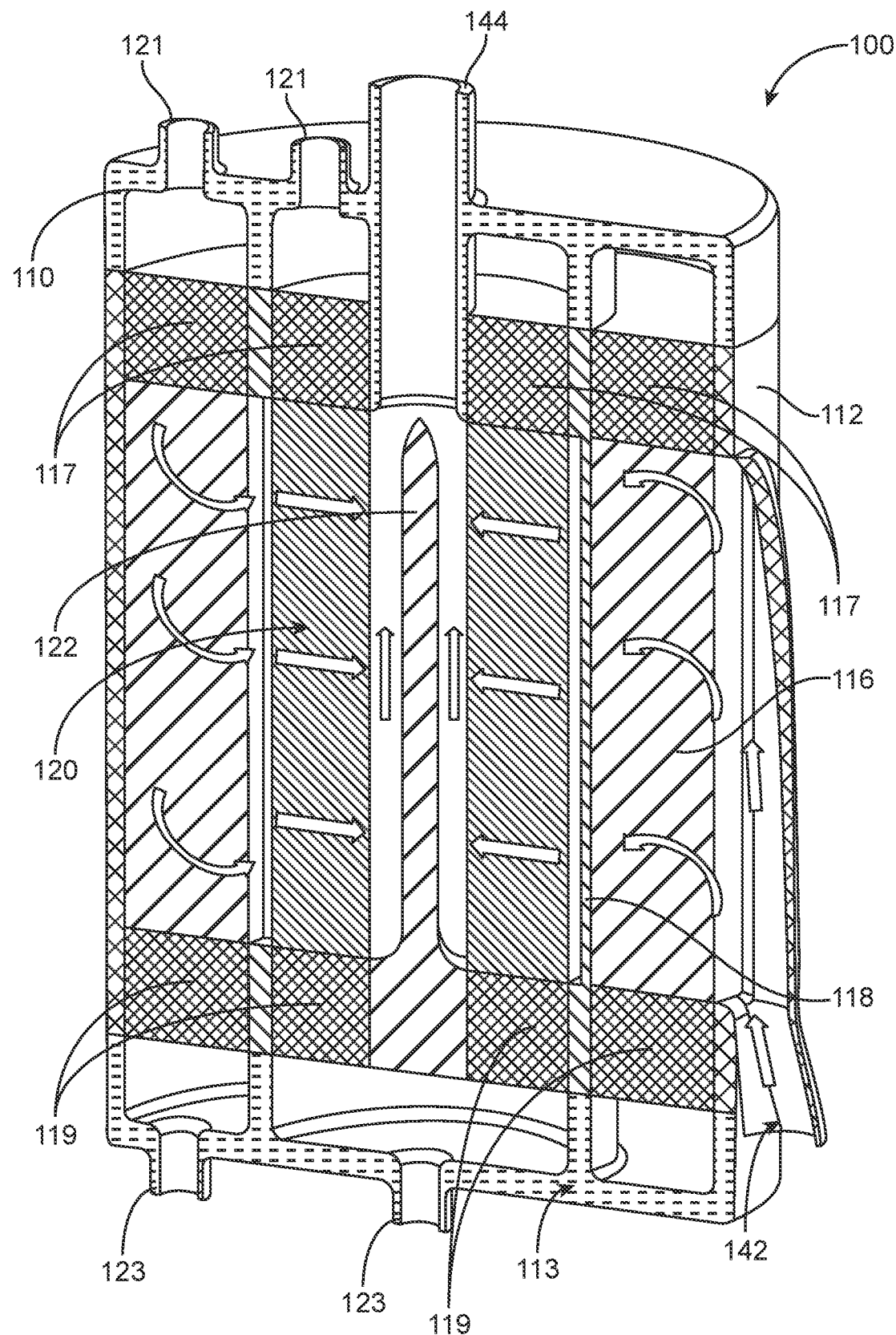
FIG. 3: Vertical cross-sectional view of the dual chamber gas exchanger of FIGS. 1 and 2 illustrating blood flow paths in a blood distributor and the inner fiber bundle and the outer fiber bundle.
Figure 4:
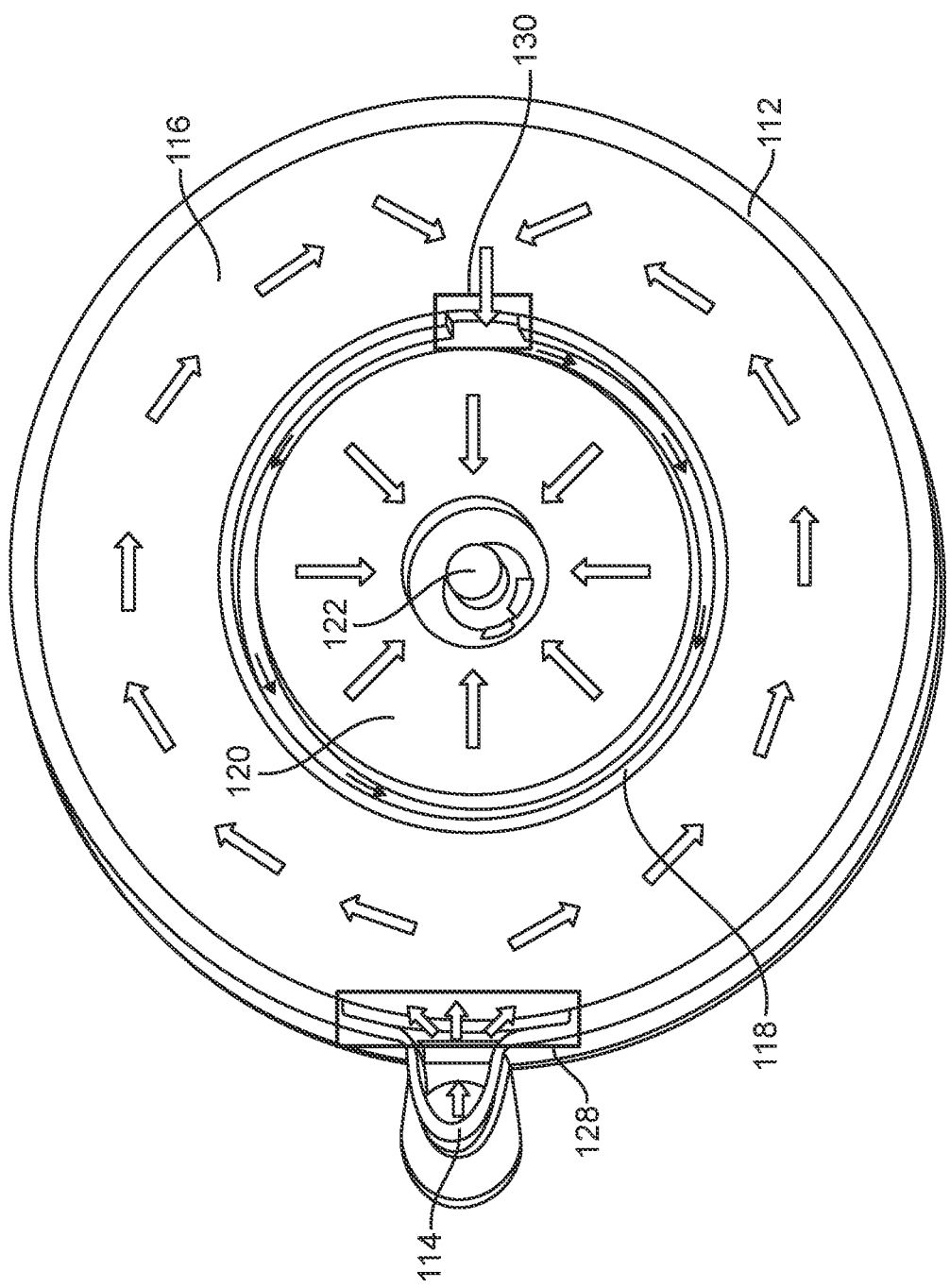
FIG. 4: Horizontal cross-sectional view of the dual chamber gas exchanger of FIGS. 1-3 illustrating a circumferential blood flow path in the outer fiber bundle starting from the distributor through Gate 1 to the outer fiber bundle and through Gate 2 to the inner fiber bundle.
Figure 5:
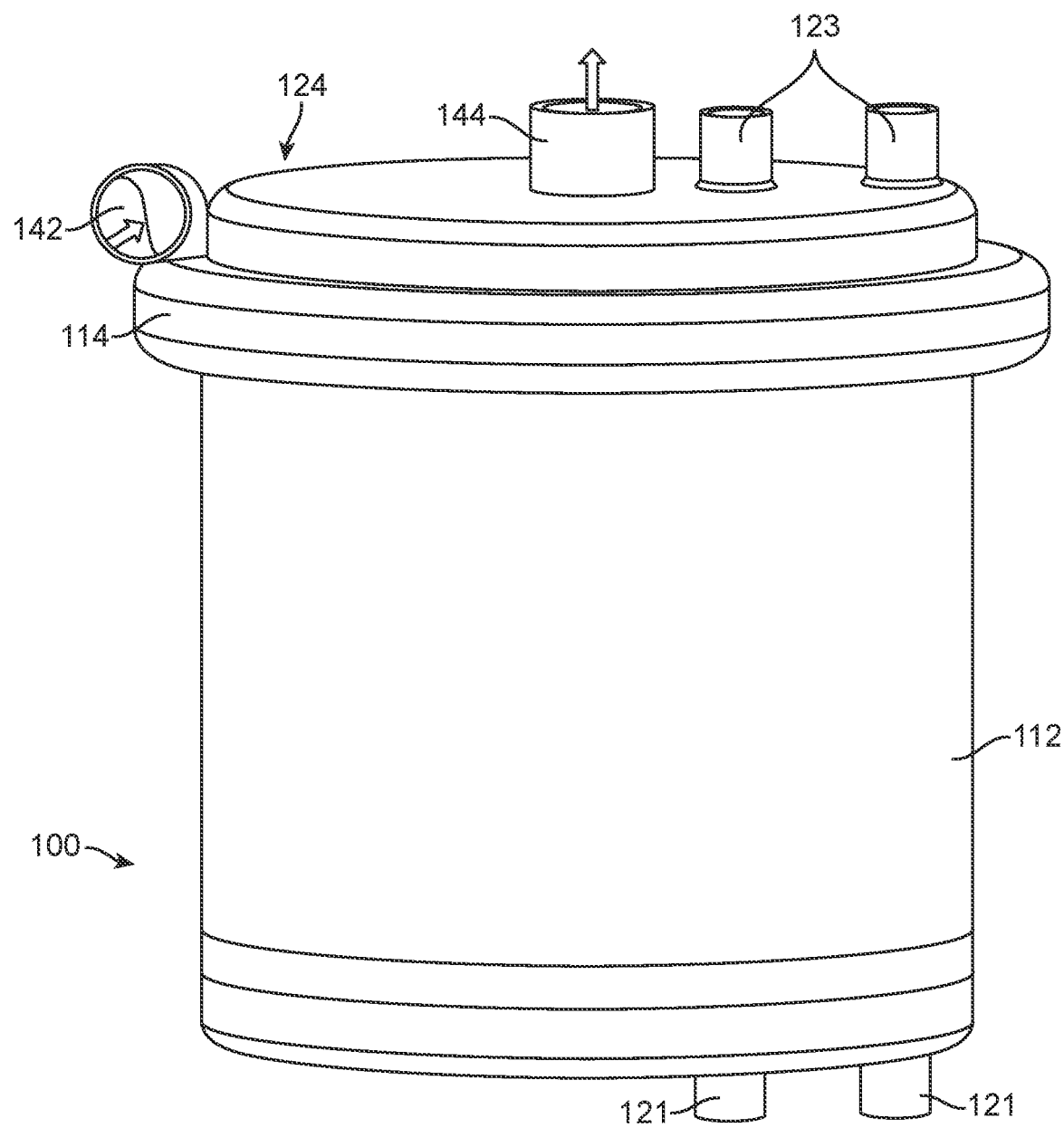
FIG. 5: Perspective view of a dual chamber gas exchanger with an axial-radial flow path, according to another embodiment of the present invention.
Figure 6:
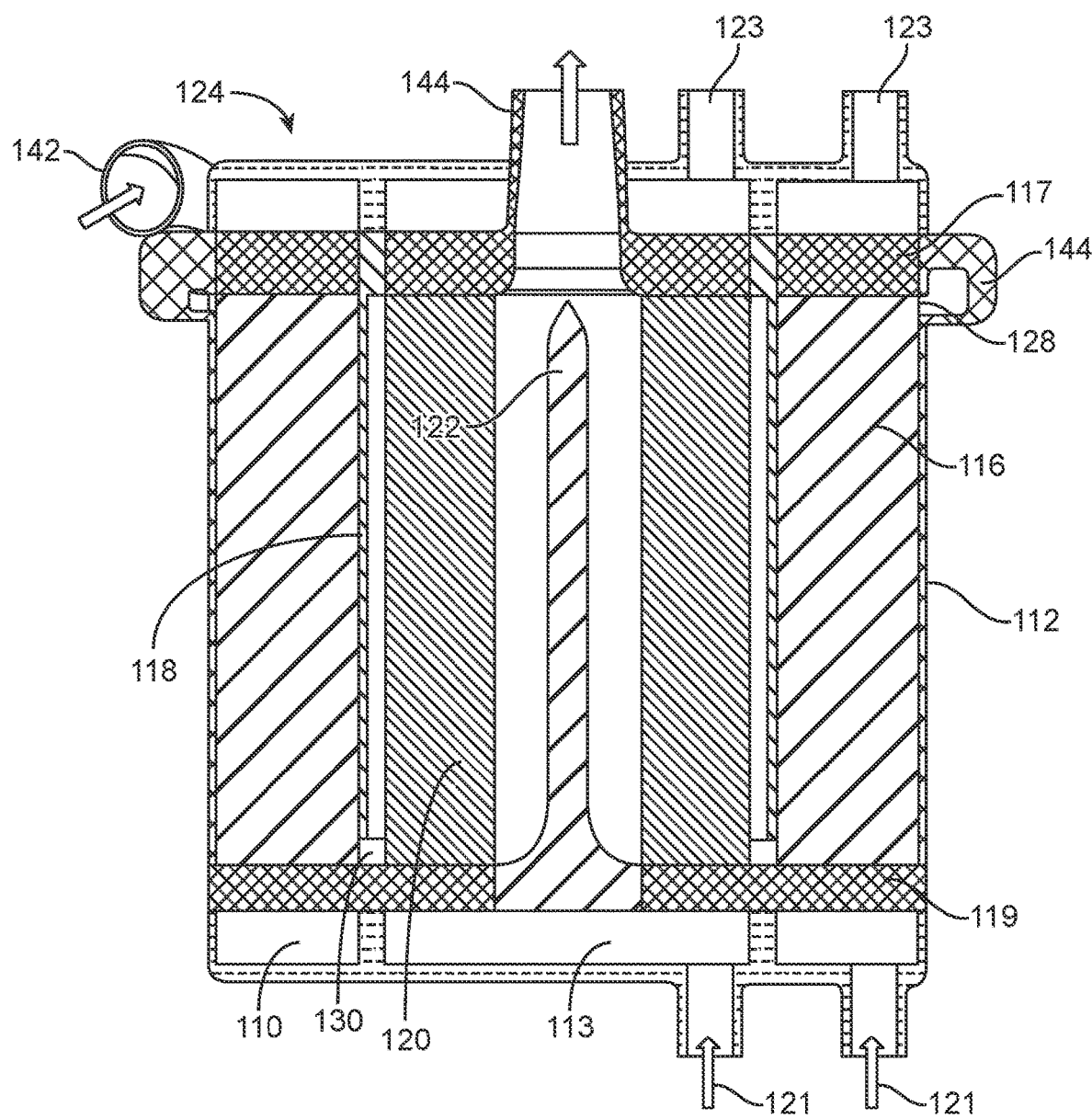
FIG. 6: Vertical cross-sectional view of the dual chamber gas exchanger of FIG. 5 with an axial flow path design in an outer fiber bundle and a radial flow path in an inner fiber bundle, two gas inlets, and two gas exhausts.
Figure 7:
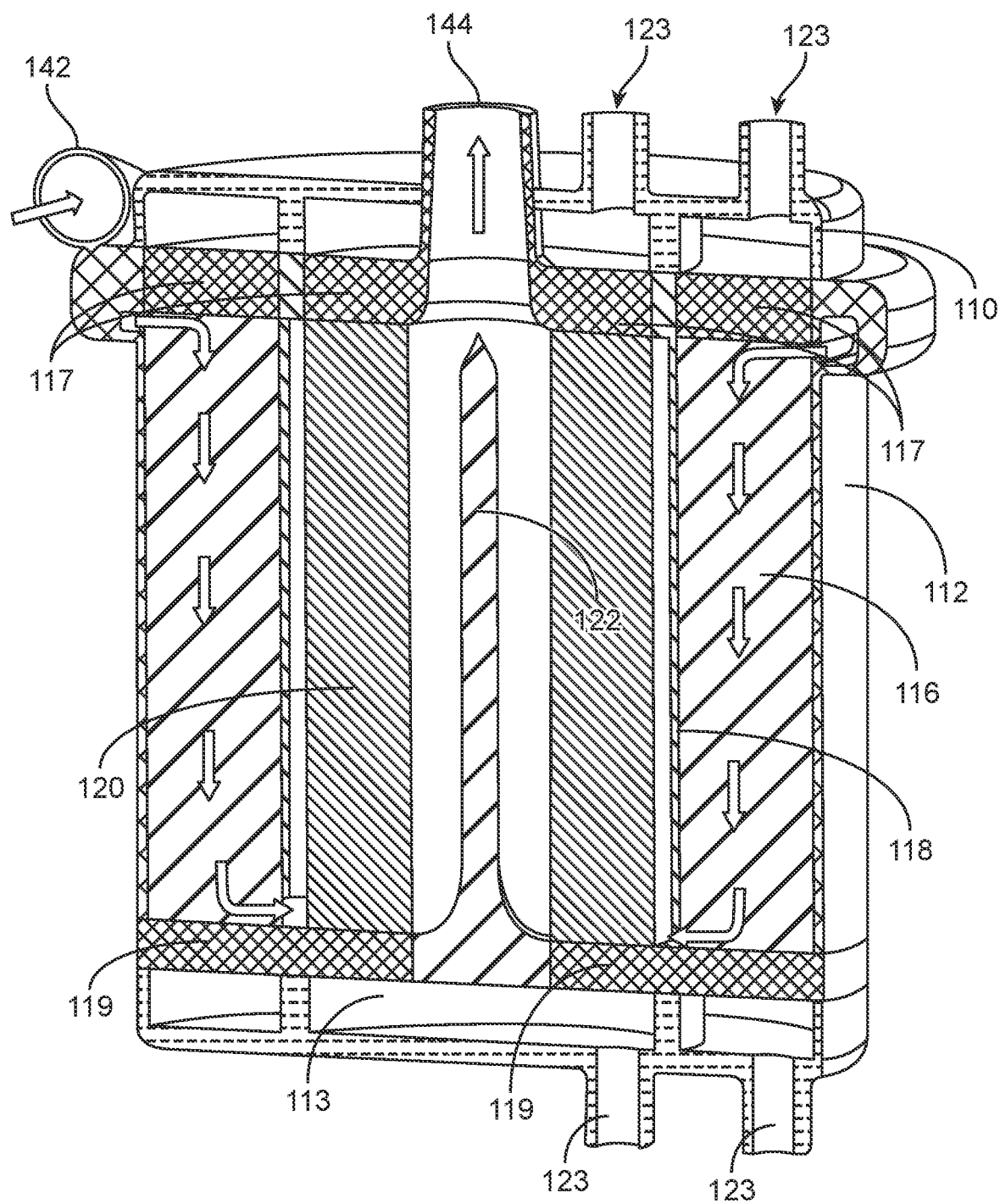
FIG. 7: Vertical cross-sectional view of the dual chamber gas exchanger of FIG. 5 illustrating blood flow paths.
Figure 8B:
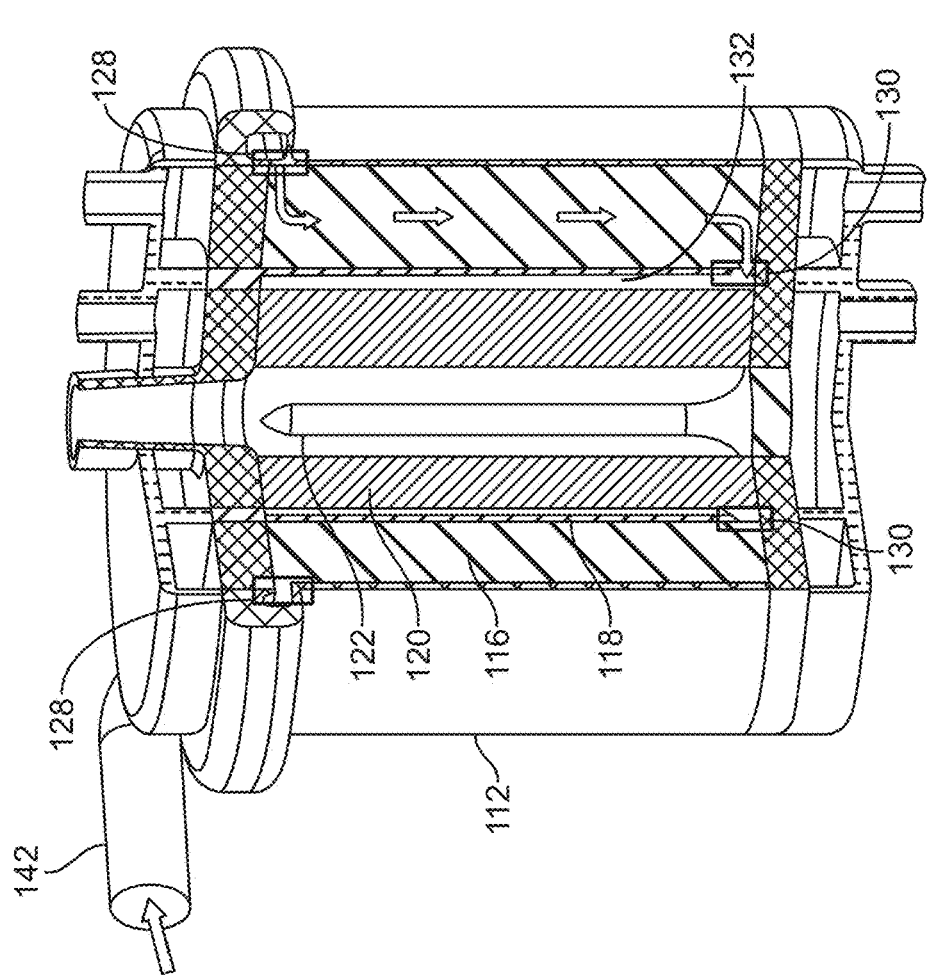
FIG. 8B is a perspective cut-away view of the dual chamber gas exchanger of FIG. 5 illustrating an axial blood flow path through Gate 1 and Gate 2 into the inner fiber bundle and exiting the dual chamber gas exchanger.
Figure 8A:
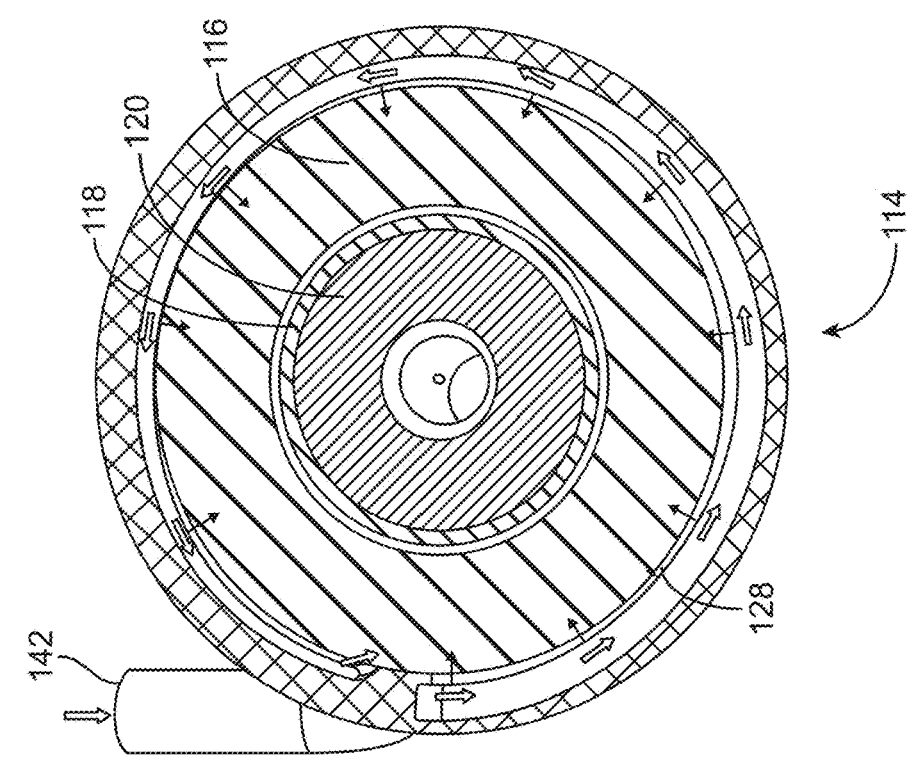
FIG. 8A is a top cross-sectional view of the dual chamber gas exchanger of FIG. 5 illustrating a spiral volute having blood flow through Gate 1.
Figure 9B:
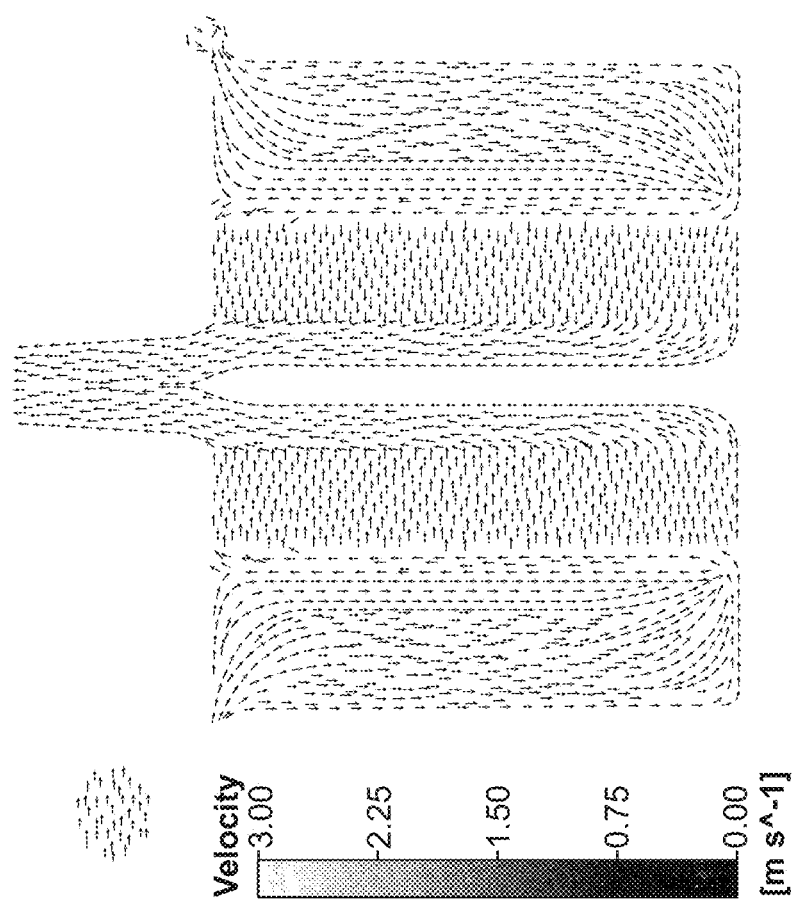
FIG. 9B is an illustration of a vertical cross-sectional view of computational fluid dynamics modelling of a blood flow field in the dual chamber gas exchanger embodiment of FIG. 5 at 6 liters per minute).
Figure 9A:
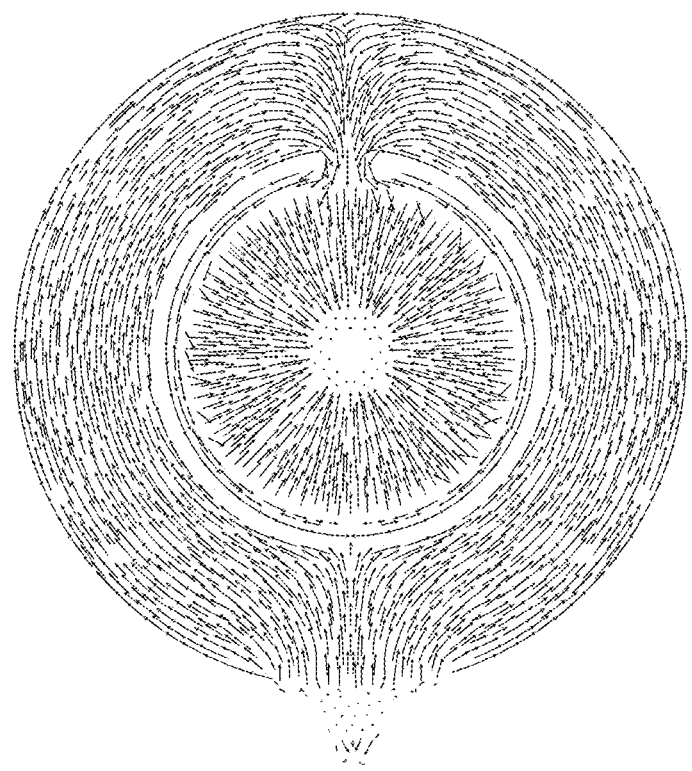
FIG. 9A is an illustration of a horizontal cross-sectional view of computational fluid dynamics modelling of a blood flow field in the dual chamber gas exchanger embodiment of FIG. 1 at 6 liters per minute.
Figures 10A, 10B:
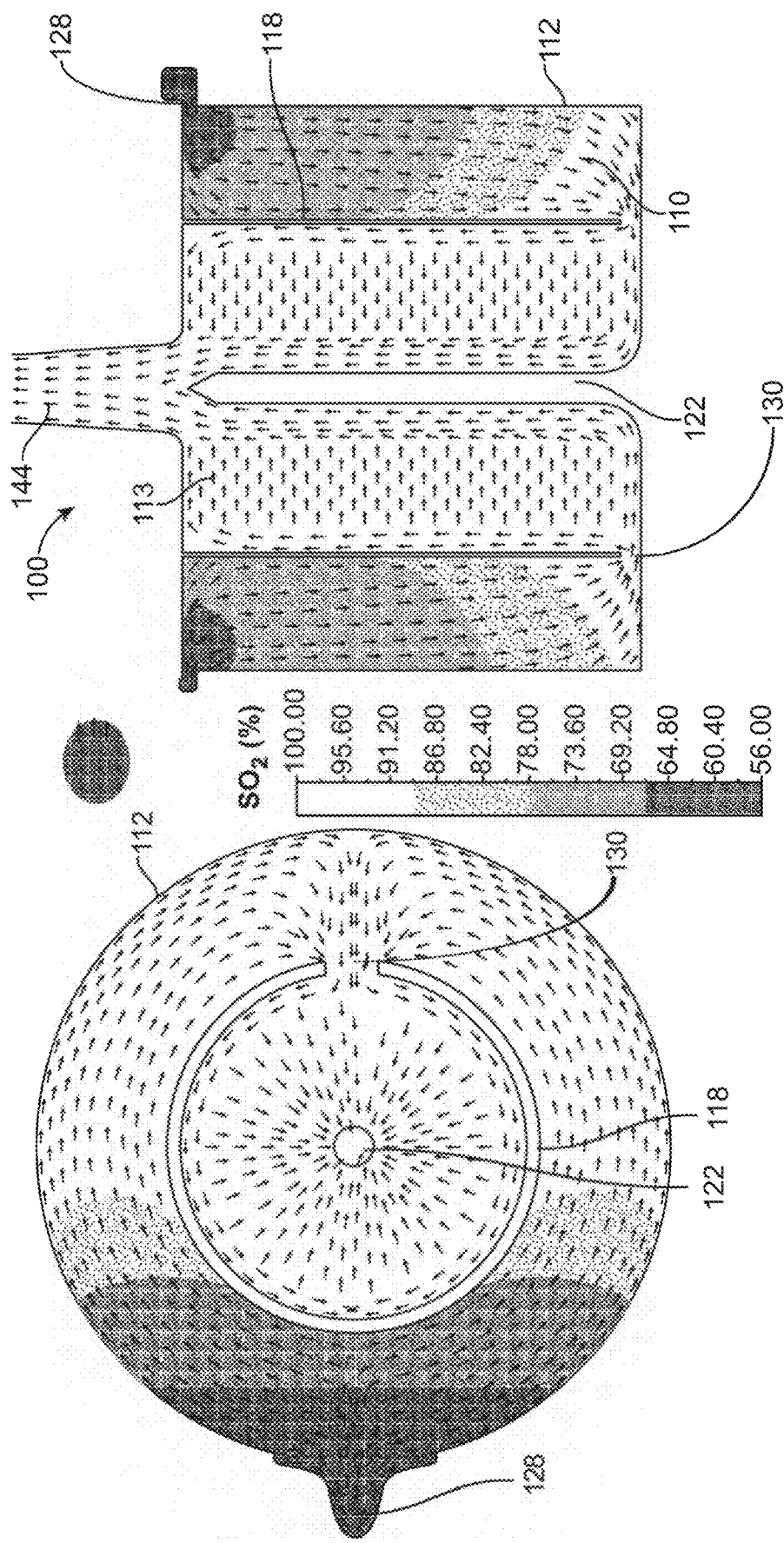
FIG. 10A is an illustration of a horizontal cross-sectional view of computational fluid dynamics modelling of the oxygen transfer process and velocity vectors of the dual chamber gas exchanger embodiment of FIG. 1 at 6 liters per minute.
FIG. 10B is an illustration of a vertical cross-sectional view of computational fluid dynamics modelling of the oxygen transfer process and velocity vectors in the dual chamber gas exchanger embodiment of FIG. 5 at 6 liters per minute).

The outer housing 112 and intermediate housing 118 is configured to form individual or mixed blood flow paths in the inner fiber bundle 120 and the outer fiber bundles 116 (FIGS. 2, 3, 6, 7, 14, 15, 17, 18, 20, and 21). In the current embodiments, various blood flow paths are possible by opening and closing either or both blood flow gates 128 and 130 (see FIGS. 2-4, 6-8B, 14-16, and 20-22). The blood flow gates are attached to the outer housing 112, the intermediate housing 118, and the blood distributor 114 that is coupled to a blood inlet 142. FIGS. 2-4 show an outer fiber bundle having a circumferential blood flow path (See arrows in FIGS. 3 and 4). The blood distributor 114 receives blood from the blood inlet 142 and is fluidly coupled to a first rectangular blood gate 128 (Gate 1) formed as a vertical slit or gap on one side of the outer housing 112, and a second rectangular blood gate 130 (Gate 2) is located at the opposite side on the intermediate housing 118. In one embodiment, the blood distributor 114 substantially uniformly discharges through Gate 1 128 into the outer fiber bundle 116 in a substantially circumferential direction through the outer fiber bundle 116 and exit through Gate 2 130 into the intermediate annular space 132 (e.g., having a cylindrical or conical-like shape) located between the inner wall of the intermediate housing 118 and the outer surface of the inner fiber bundle 120. As a further alternative, the dual chamber gas exchanger 100 is configured to filter particulates in the blood. For example, the dual chamber gas exchanger 100 can include a filter, such as a depth filter, reticulated foam, microporous filtration, filtration mediums, or the like.

In another embodiment of the dual chamber gas exchanger 100, shown in FIGS. 6-8B, the outer fiber bundle 116 has an axial blood flow path. The blood distributor 114 is configured in the shape of a spiral-like volute having a cross-sectional area that is gradually decreasing (see e.g., FIGS. 14-16, 17-19, and 20-22). FIGS. 5-8B illustrate that the blood distributor 114 generally encircles a top end of the outer housing 112 and attaches to the first blood gate 128 (Gate 1) that is generally like a thin slot. The second thin slot blood gate 130 (Gate 2) is located at an end of the intermediate housing 118 that is opposite to Gate 1 128. The spiral-like volute blood distributor 114 gradually discharges blood circumferentially (e.g., 360 degrees) into the top end of the outer fiber bundle 116 through Gate 1 128. Blood flows in the axial direction to exit the outer fiber bundle 116 and enter the intermediate annular space 132 between the inner wall of the intermediate housing 118 and the outer surface of the inner fiber bundle 120 through Gate 2 130. The flow path through the inner fiber bundle 120 is radial, which increases biocompatibility and gas exchange efficiency and has low pressure loss.

Still referring to FIGS. 6-8B, the intermediate annular space 132 is generally formed between the inner wall of the intermediate housing 118 and the outer surface of the inner fiber bundle 120, and has a generally uniform pressure distribution (e.g., prior to blood entering the inner fiber bundle 120). The blood has a generally uniform pressure distribution that causes blood to flow in a substantially uniform radially inward direction through the fiber membranes of the inner fiber bundle 120 (see FIGS. 3, 4, 7, 8A and 8B, 18, and 19). Computational fluid dynamics analysis demonstrates the substantially uniform flow and the substantially uniform oxygen transfer in the inner fiber bundle 120 and outer fiber bundle 116 (FIGS. 9A, 9B, 10A, and 10B).

Thus, the inner fiber bundle 120 and the outer fiber bundle 116 may be configured for various blood flow paths (e.g., circumferential, axial, and/or radial), depending on the clinical application. For example, one embodiment of the dual chamber gas exchanger 100 includes the inner fiber bundle 120 having a radial flow path and the outer fiber bundle 116 having a circumferential flow path (see FIGS. 2-4). As further example, another embodiment of the dual chamber gas exchanger 100 includes the inner fiber bundle 120 having a radial flow path and the outer fiber bundle 116 having an axial flow path (see FIGS. 6-8B). As a still further example, another embodiment of the dual chamber gas exchanger 100 includes the inner fiber bundle 120 having a circumferential flow path and the outer fiber bundle 116 having a radial flow path (see FIGS. 14-16). As a yet further example, another embodiment of the dual chamber gas exchanger 100 includes the inner fiber bundle 120 and the outer fiber bundle 116 having a radial flow path (see FIGS. 17-19). As a further example, another embodiment of the dual chamber gas exchanger 100 includes the inner fiber bundle 120 having an axial flow path and the outer fiber bundle 116 having a radial flow path (see FIGS. 20-22). Other combinations and configurations of flow paths are feasible within the dual chamber gas exchanger 100.

Referring to FIGS. 2, 3, 6, 7, 14, 15, 17, 18, 20, and 21, the inner fiber bundle 120 and the outer fiber bundle 116 of the current embodiment are cylindrical annulus that include many hollow membrane fibers, or microporous hollow fibers, e.g., having pore sizes that are generally less than 0.1 micron in diameter. The hollow membrane fibers of the current embodiment are commercially available and have an outer diameter approximately between 250 microns and 400 microns, and a wall thickness approximately between 30 microns and 50 microns, although hollow fiber membranes having other outer diameters and wall thicknesses are feasible with the dual chamber gas exchanger 100. In another embodiment, the hollow membrane fibers are configured to be anti-thrombogenic, for example having an anti-thrombogenic coating (e.g., heparin or a functional equivalent). Alternatively, the hollow membrane fibers may be microporous membranes to filter blood components, such as for blood dialysis.

The porosity (or void ratio) of each inner fiber bundle 120 and outer fiber bundle 116 is generally determined by the desired pressure loss across the inner fiber bundle 120 and the outer fiber bundle 116. In the current embodiment, the porosity ranges approximately between 0.4 and 0.7. Alternatively, coated or skinned hollow fibers may be used to permit oxygen and carbon dioxide diffusion through a non-porous skin layer of the outer wall of the membrane fibers. The hollow membrane fibers are typically available commercially in a tape configuration whereby individual hollow membrane fibers are arranged to a predetermined configuration (i.e. parallel straight or bias, multi-directional, woven, spaced, etc.) permitting tape wrapping to form a cylindrical or conical-like bundle configuration. Alternatively, the hollow fiber membranes can be wrapped or wound (e.g., like a spool of kite-string). The hollow membrane fibers are attached to each of the lower potting 119 and upper potting 117 (see FIGS. 2, 3, 6, 7, 14, 15, 17, 18, 20, and 21). For example, in the current embodiment, the ends of the inner fiber bundle 120 and the outer fiber bundle 116 are trimmed to open inner lumens of the membrane fibers and cast-potted using a polymer (e.g., urethane, epoxy, or the like). The sweep gas is distributed through the inner lumens between the upper potting 117 and the lower potting 119.

In one embodiment, the dual chamber gas exchanger 100 includes a heat exchanger that is configured to control blood temperature. The heat exchanger may include a cylindrical annulus of heat exchange elements around at least one of the inner fiber bundle 120 or outer fiber bundle 116. The cylindrical annulus is formed of a plurality of capillaries that are potted to one of the inner fiber bundle 120 or the outer fiber bundle 116. The heat exchanger capillaries can be formed of biocompatible metals, polymers, or the like. The capillaries have lumens that are opened to form a separated flow path. The heat exchanger further includes a sweep gas chamber and a heat transfer medium chamber that are configured to control heat of the sweep gas and heat transfer medium, respectively. In the one embodiment, the sweep gas chamber and the heat transfer medium chamber are disposed on top of the outer housing 112 above the upper potting 117, however, in another embodiment the sweep gas chamber and the heat transfer medium chamber are disposed below the outer housing 112 above the lower potting 119. The temperature of the blood is controlled by varying a flow rate and temperature of the heat transfer medium as it flows through the heat exchanger capillaries and the hollow membrane fibers.

In an alternative embodiment, a plurality of hollow tubes are configured for heat transfer, rather than configuring the hollow fiber membranes as heat exchangers. Such a configuration uses a temperature-controlled fluid, such as water, to affect blood temperature change.

The gas inlet 121 (FIGS. 1-3 and 5-7) is configured to operate at a low pressure while providing uniform sweep gas in the outer fiber bundle 116 and/or the inner fiber bundle 120. The gas inlet 121 includes inflow and outflow connectors that are sized to achieve desired blood flow rates and pressures. For example, the dual chamber gas exchanger 100 can include typical ¼" or ⅜" barbed fittings that receive standard device-assisted extracorporeal circulation tubing.

One embodiment of the dual chamber gas exchanger includes an arterial sample port 136 and a venous sample port 138 (FIGS. 1 and 2) that are configured to permit operators to collect blood samples from the dual chamber gas exchanger 100 (e.g., using syringes, traditional stopcocks, obturator-type sample ports, and the like). The arterial sample port 136 and the venous sample port 138 are further configured to allow an operator to sample blood before the blood flows into the inner fiber bundle 120 and/or outer fiber bundle 116, and after the blood flows exiting from the inner fiber bundle and 120/or outer fiber bundle 116 to control various parameters (e.g., blood flow rates, gas transfer rates and pH for the control of oxygen concentration).

In one embodiment, dual chamber gas exchanger 100 may be configured to remove air bubbles from the blood. One embodiment can include an outer vent port 140 (FIGS. 1, 3, 5-7, 12-15, and 17) positioned near a portion of the dual chamber gas exchanger 100 where air bubbles generally accumulate. For example, the outer vent port 140 can be located at the outer wall of the outer housing 112 near the upper potting 117 (FIG. 2). Furthermore, other embodiments of the dual chamber gas exchanger 100 may include an inner vent port that is located near the top of the intermediate housing 118, such as the upper potting 117 of the inner fiber bundle 120 to remove air bubbles. Air bubbles typically result from trapped air that is not adequately removed during priming, by broken hollow membrane fibers, or from excessive negative pressure applied to blood that forces gases out of solution.

Figure 23B:
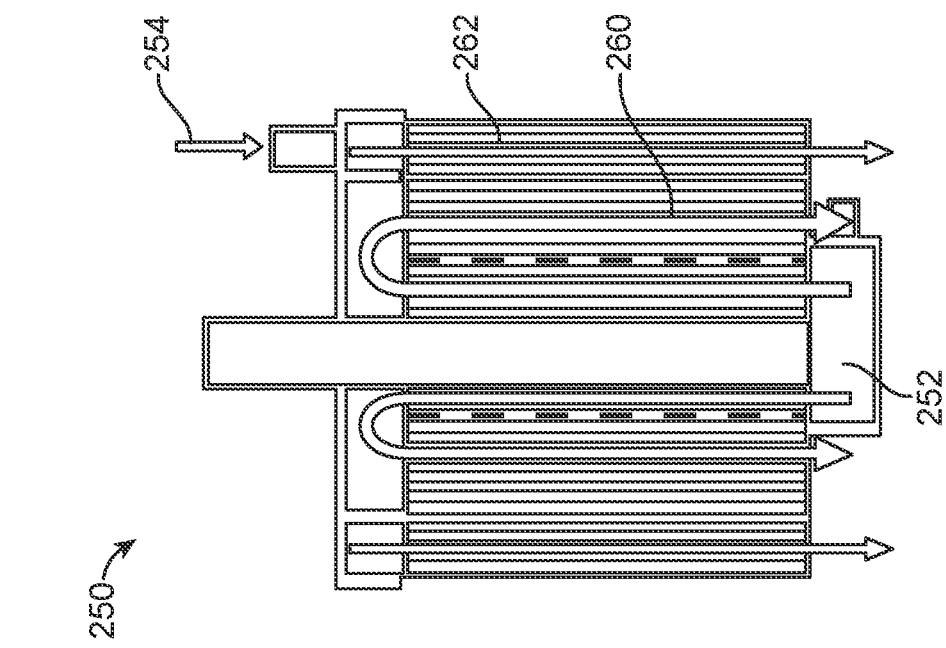
FIGS. 23A and 23B: A schematic of alternative gas flow paths in a dual chamber gas exchanger, according to alternative embodiments of the present invention, in which an exhausted oxygen-rich sweep gas from one of an inner fiber bundle or an outer fiber bundle mixes with atmospheric air for use as a sweep gas in the other of the inner fiber bundle or outer fiber bundle (FIG. 23A); and in which each sweep gas is used for the inner fiber bundle and the outer fiber bundle separately (FIG. 23B).
Figure 23A:
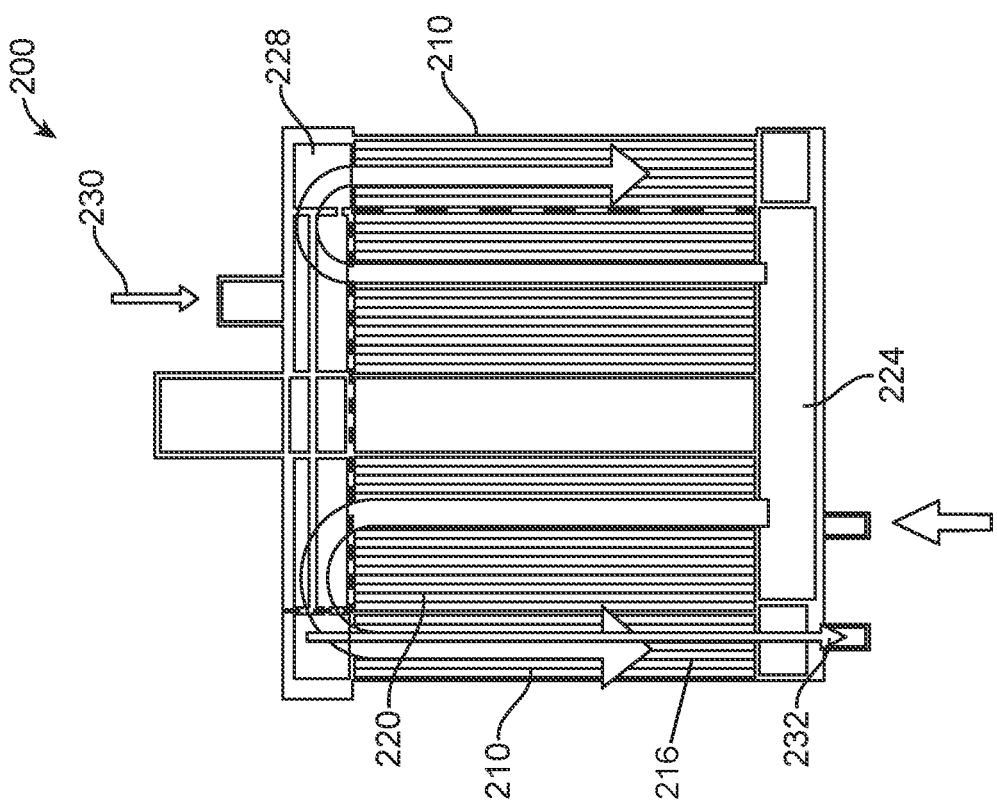

As shown in FIGS. 23A and 23B, an oxygenator in accordance with the principles of the present invention may be configured with an oxygen-rich gas passing through one portion of a gas exchange fiber bundle and an air or other oxygen-depleted stripping gas passing through another portion of the fiber bundle. Optionally, such oxygenators may have gas flow paths in which an exhausted oxygen-rich sweep gas from one of an inner fiber bundle or an outer fiber bundle mixes with atmospheric air for use as a sweep gas in the other of the inner fiber bundle or outer fiber bundle.

As shown in FIG. 23A, an exchanger 200 comprising a fiber bundle 210 is configured to reuse the oxygen-rich exhausted sweep gas from an inner fiber bundle 220 in an outer fiber bundle 216. For example, oxygen from an external source, such as a tank, or an oxygen concentrator is diffused into the inner fiber bundle 220 through a lower portion or plenum 224 of the dual gas chamber. The oxygen-rich gas is partially depleted of oxygen as it passes through the inner fiber bundle 220 and then passes through an upper plenum 228 where it is mixed with atmospheric air entering through inlet 230. The combined gas flows then pass down the outer fiber bundle 216 to remove or "strip" carbon dioxide from the blood entering the fiber bundle 210 horizontally in any of the flow paths previously described. The combined gases, although not oxygen rich, will nonetheless provide an initial stage of oxygenation in addition to stripping the carbon dioxide. Oxygenation is completed in the inner fiber bundle 220 where the blood is exposed to a gas having a higher oxygen concentration. The sweep gas is ventilated into the atmosphere from a bottom portion of the dual gas chamber 232. Thus, the gas flow rate and oxygen utilization efficiency for mixed atmospheric and oxygen sweep gas can be increased because atmospheric air is generally abundant and simple to use in the dual chamber gas exchanger 200.

Referring to FIG. 23B, an alternative embodiment of a dual chamber gas exchanger embodiment 250 may be configured to pass an oxygen-rich sweep gas 252 through an inner fiber bundle 260 only and only pass atmospheric air 254 through an outer fiber bundle 262 only. The arrangement of plenums and isolation barriers will be made accordingly.

Figure 24:
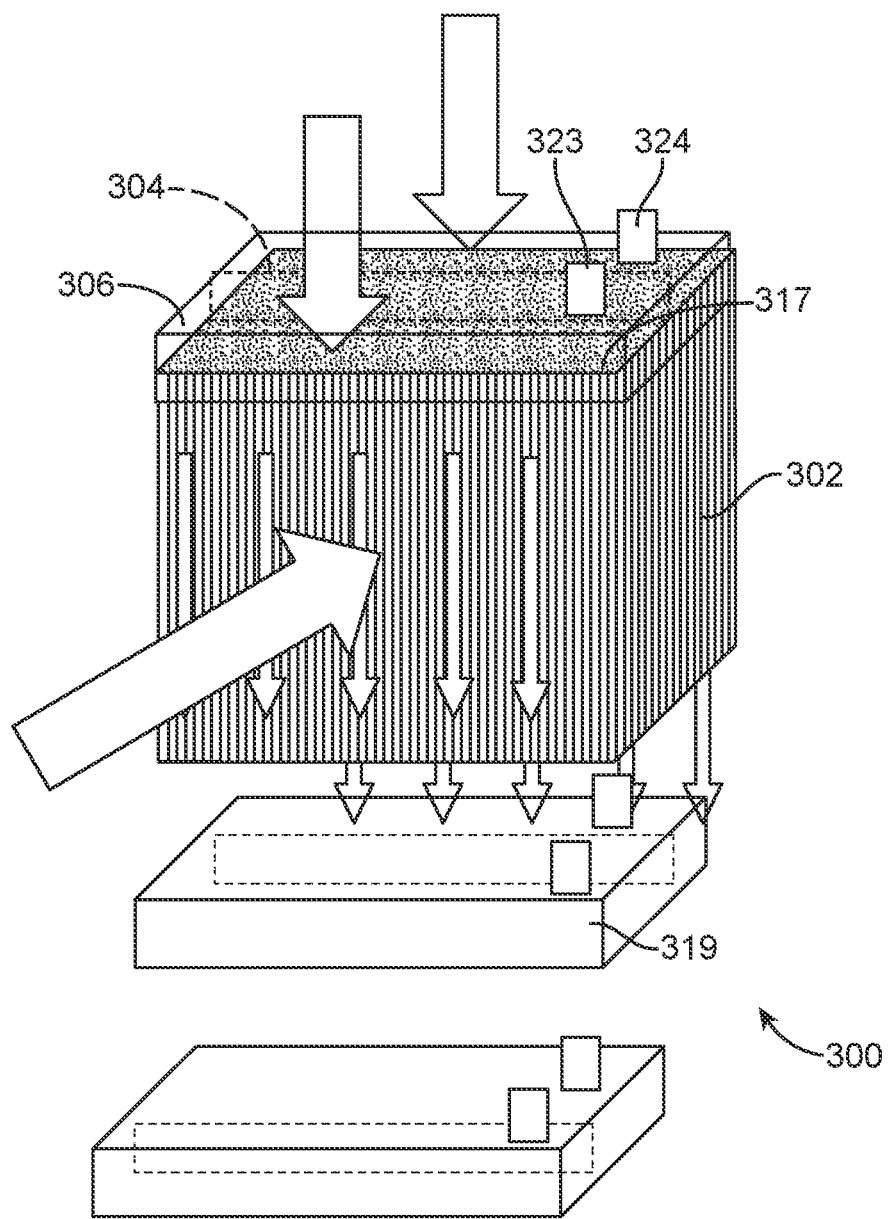
FIG. 24: Blood flow path and gas flow paths in a dual chamber gas exchanger having a square fiber bundle and two gas inlets, according to another embodiment of the present invention.

In FIG. 24, an oxygenator 300 has a rectangular shape with separate gas inlets 323 and 324 at the top and a rectangular fiber bundle 302 placed between an upper potting 317 and a lower potting 319. In contrast to previous embodiments, the fiber bundle 302 is free from barriers that create isolated air flow regions therein. Gas flow through the fiber bundle 302 is controlled by a moveable partition 304 which is positioned in a gas inlet region 306 above the upper potting 317. The gas inlets 323 and 324 release gas on opposite sides of the partition 304 and may be connected to different gas sources, such as air and oxygen respectively. Moving the partition 304 will thus adjust the fiber areas to which each gas is exposed. For example, blood flowing in the direction of the horizontal arrow in FIG. 24 would first be exposed to the gas entering through inlet 323, which could be an air or other low oxygen stripping gas. After carbon dioxide is at least partially stripped, the blood could be exposed to an oxygen rich gas delivered through inlet 324 for complete oxygenation. Blood of course is flowing vertically in the direction of the vertical arrows. In some embodiments, the partition 304 could be fixed. While adjustability of the fiber areas would be lost, the efficiency of stripping carbon dioxide from the blood using air or other low oxygen gas and achieving final oxygenation with pure or other high oxygen gas would be retained.

Figure 25:
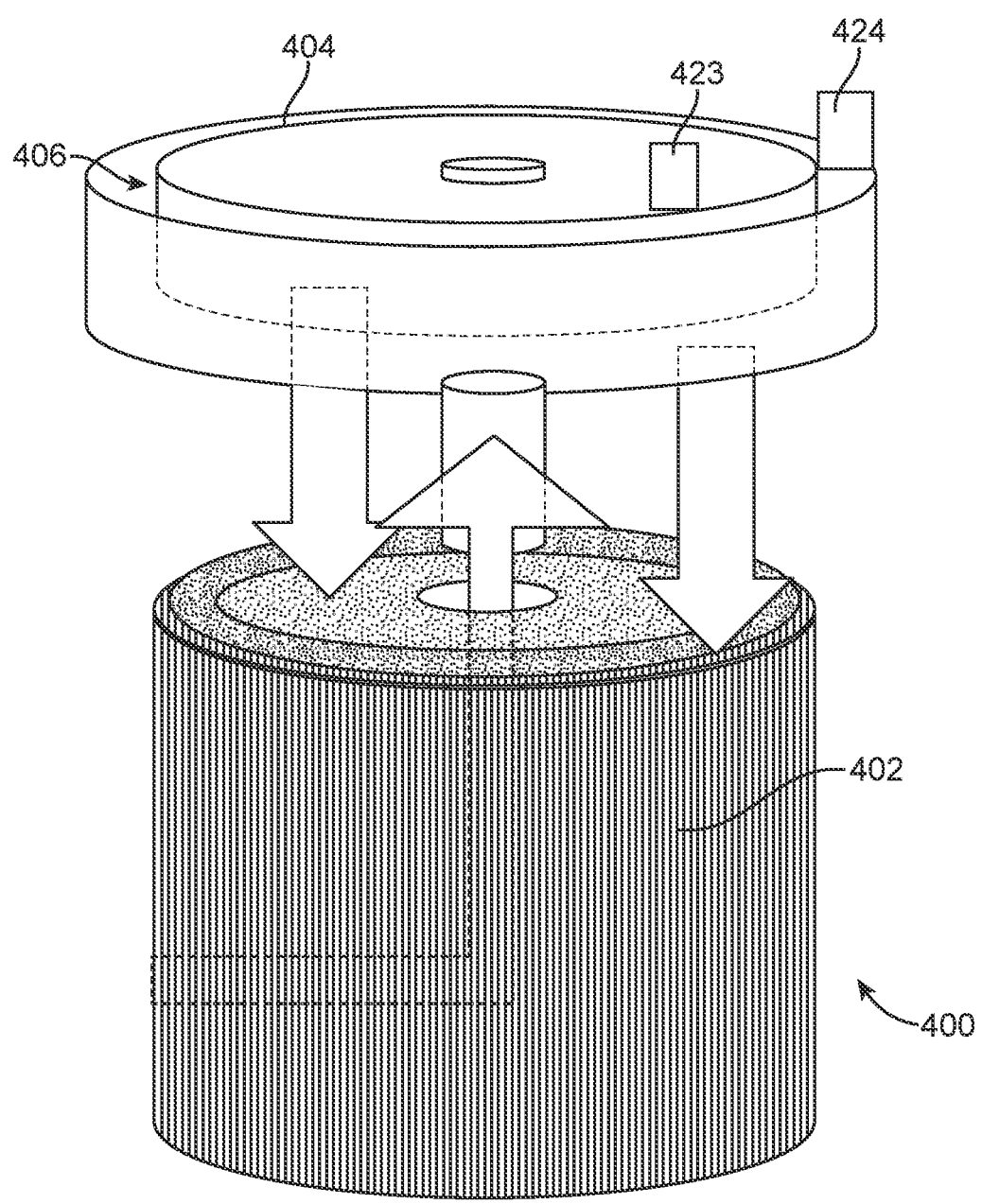
FIG. 25: Blood flow path and gas flow paths in another embodiment of a dual chamber gas exchange having regions within the fiber bundle divided by a moveable wall in a cylindrical gas inlet manifold.

In a further embodiment, as illustrated in FIG. 25, an oxygenator 400 has a cylindrical shape with separate gas inlets 423 and 424 at the top and an annular fiber bundle 402 placed between an upper potting and a lower potting (not shown). A circular partition 404 having an adjustable diameter is positioned in a gas inlet region 406 above the upper potting. The gas inlets 423 and 424 will be positioned to lie outside of and inside of the partition 406 and may be connected to different gas sources, such as air and oxygen respectively. Adjusting the diameter of the partition 404 will adjust the fiber areas to which each gas is exposed. For example, blood flowing in the direction of the horizontal arrow in FIG. 24 would first be exposed to the gas entering through inlet 423, which could be an air or other low oxygen stripping gas. After carbon dioxide is at least partially stripped, the blood could be exposed to an oxygen rich gas delivered through inlet 424 for complete oxygenation. Blood of course is flowing vertically in the direction of the vertical arrows. In some embodiments, the partition 404 could be fixed. While adjustability of the fiber areas would be lost, the efficiency of stripping carbon dioxide from the blood using air or other low oxygen gas and achieving final oxygenation with pure or other high oxygen gas would be retained.

Figure 26B:
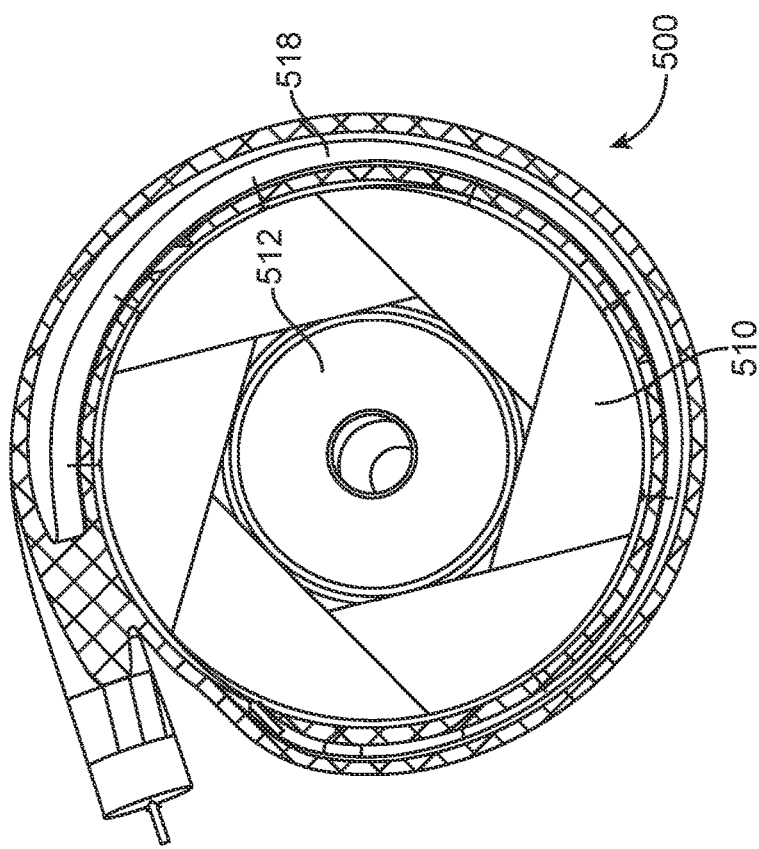
FIG. 26B: Horizontal cross-sectional view of a variable partition mechanism similar to that of FIG. 26A with a spiral volute.
Figure 26A:
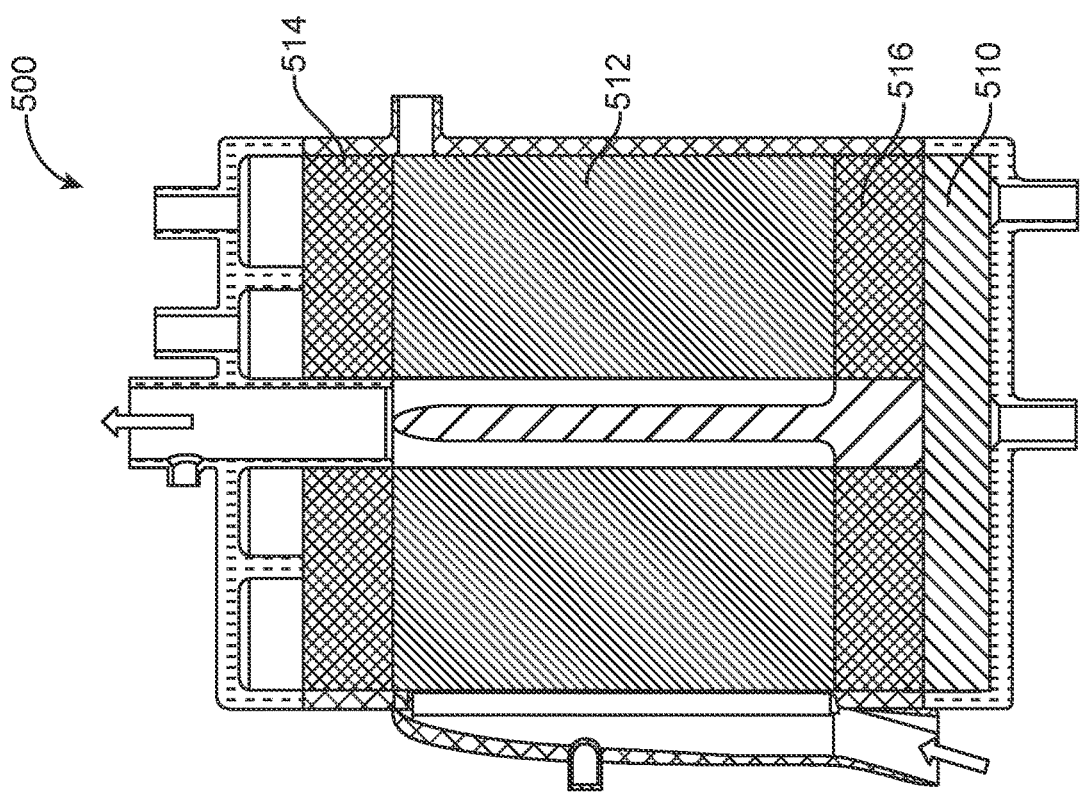
FIG. 26A: Vertical cross-sectional view of a dual chamber gas exchanger with an alternative partition mechanism.

In yet another embodiment of the present invention, shown in FIGS. 26A and 26B, a dual chamber gas exchanger 500 (similar to the dual chamber gas exchangers 100 as described above) is further configured to vary sweep gas exchange rates independently of the sweep gas concentrations (e.g., without varying the flow rates and/or concentration of the sweep gases). The dual chamber gas exchanger 500 includes a partition mechanism 510, which in one embodiment is an adjustable aperture such as an iris mechanism that is configured to vary a portion of the surface area of the dual chamber gas exchanger membrane 512 that is in contact with blood for transferring oxygen and also to vary a portion of the surface area of the dual chamber gas exchanger membrane 512 that is in contact with blood for carbon dioxide removal, as described above.

The partition mechanism 510 varies the portions of sweep gases for gas exchange by varying access or fluid communication of the sweep gases into separate paths through different regions within the fiber bundle without a physical chamber wall (e.g., intermediate housing). Varying access by controlling and adjusting the areas of the gas flow paths (e.g., portion of the hollow fiber membrane exposed to the inlet gas flow) in which the sweep gases are exposed to a patient's blood flow allows a clinician to more accurately and efficiently match the patients' requirements (e.g., metabolic needs).

In the illustrated embodiment, the partition mechanism 510 is a mechanical mechanism (FIG. 26B), such as an iris-type or shutter-type mechanism that is configured to vary an opening area to control the flow gas. In other embodiments, the opening area may have a circular or hexagonal-like shape, such that the opening area is varied by varying a diameter or width. The partition mechanism 510 is fluidly coupled with at least one of the upper potting 514, lower potting 516. A spiral volute may distribute the gas to the fiber bundle (FIG. 26B) or alternatively, a vrticluscal inlet (as provided in prior embodiments) may be used (FIG. 26A). The partition mechanism 510 can be a valve or plurality of valves, such as an array or series of valves that controls fluid access to various flow paths, such as described above. The opening area of the partition mechanism 510 is controlled by a controller, such as by the blood pump controls described above. The partition mechanism 510 thus allows the dual chamber gas exchanger 500 to control the mixture and rate of sweep gases into portions of the dual chamber gas exchanger membrane 512 exposed to and in fluid contact with the patients' blood to transfer oxygen and to remove carbon dioxide.

The present invention is a dual chamber gas exchanger device. The dual chamber gas exchanger is configured to increase the efficiency of gas exchange, such as with oxygen and carbon dioxide, relatively low pressure loss, good biocompatibility, and unique flexibility but require minimal volume and blood contacting surface. The dual chamber gas exchanger increases options for optimal blood flow paths and efficiency of gas transfer in an inner fiber bundle and an outer fiber bundle. The dual chamber gas exchanger also reduces the amount of oxygen required for oxygen transfer to the blood and carbon dioxide removal from the blood simultaneously. The reduced oxygen requirements and reduced size and weight of the dual chamber gas exchanger device further increases the variety of applications of use. For example, the dual chamber gas exchanger can operate with a small portable oxygen concentrator having low power consumption to provide a sweep gas for oxygen transfer and carbon dioxide removal that is required in ambulatory uses and the like.

Additionally, the dual chamber gas exchanger is further configured to enhance gas exchange using an active mixing mechanism. The active mixing mechanism uses an inner fiber bundle and an outer fiber bundle to decrease the boundary layer effect of blood flow and improve gas exchange efficiency. The intermediate housing and the inner fiber bundle form a cylindrical or conical-like space that is configured to increase the interaction of blood with membranes by enabling high momentum blood flow in the space between the membrane outer surface and inner housing wall, such that blood encounters lower flow resistance, increased turbulence, and increased mixing after passing through the outer fiber and before entering the inner fiber bundle. Thus, the dual chamber gas exchanger mixes the blood without introducing unnecessary high shear rates or stagnant zones as in typical blood oxygenating devices. Moreover, the dual chamber gas exchanger includes fewer components than typical blood oxygenating devices. The dual chamber gas exchanger is configured to increase maintainability and operability, compared to typical blood oxygenating devices, by increasing access to joints and bonding area.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A blood oxygenator comprising:
   a housing comprising a blood inlet, a blood outlet, a stripping gas inlet, an oxygenation gas inlet, and at least one gas outlet; and
   an oxygenator fiber bundle disposed within the housing and configured so that blood flows through a blood flow region in the oxygenator fiber bundle in a predetermined path from the blood inlet to the blood outlet;
   wherein the stripping gas inlet is configured to direct a flow of stripping gas through a stripping region of the oxygenator fiber bundle to the at least one gas outlet and the oxygenation gas inlet is configured to direct a flow of oxygenation gas through an oxygenation region of the oxygenator fiber bundle to the at least one gas outlet; and
   wherein the stripping gas region of the oxygenator fiber bundle is upstream of the oxygenation region of the oxygenator fiber bundle.

2. The blood oxygenator of claim 1, wherein the fiber bundle is cylindrical and at least a portion of the blood flow path is radially inward or radially outward.

3. The blood oxygenator of claim 1, wherein the fiber bundle is cylindrical and at least a portion of the blood flow path follows an annular path.

4. The blood oxygenator of claim 1, wherein at least a portion of the blood flow path is unidirectional across the oxygenator fiber bundle.

5. The blood oxygenator of claim 1, wherein the fiber bundle is cylindrical and an outer portion of the blood flow path follows an annular path and an inner portion follows a radially inward path.

6. The blood oxygenator of claim 5, wherein the blood inlet feeds the outer portion and the inner portion feeds the blood outlet.

7. The blood oxygenator of claim 6, wherein the stripping region is disposed at least in part in the outer portion of the blood flow path and the oxygenation region is disposed at least in part in the inner portion of the blood flow path.

8. The blood oxygenator of claim 5, wherein the blood inlet feeds the inner portion and the outer portion feeds the blood outlet.

9. The blood oxygenator of claim 8, wherein the stripping region is disposed at least in part in the inner portion of the blood flow path and the oxygenation region is disposed at least in part in the outer portion of the blood flow path.

10. The blood oxygenator of claim 5, further comprising a cylindrical wall separating the outer portion and the inner portion of the cylindrical fiber bundle, wherein blood flows from the blood inlet through an axial opening in the housing into the outer portion of the fiber bundle and flows annularly through the outer portion of the fiber bundle to and through an axial opening in the cylindrical wall into a distribution ring surrounding the inner bundle from where the blood flows radially inwardly through the inner portion of the fiber bundle to an axial collection region along a center axis of the inner portion of the fiber bundle.

11. The blood oxygenator of claim 1, wherein the oxygenation fiber bundle has a cross-sectional area and the stripping region that receives the stripping gas from the stripping gas inlet has an inlet area that comprises from 20% to 80% of the cross-sectional area and the oxygenation region that receives the oxygenation gas from the oxygenation gas inlet has an inlet area that comprises from 80% to 20% of the cross-sectional area.

12. The blood oxygenator of claim 11, further comprising a manifold divider which directs the stripping gas from the stripping gas inlet to the stripping region of the oxygenator fiber bundle and directs the oxygenation gas from the oxygenation gas inlet to the oxygenation region of the oxygenator fiber bundle.

13. The blood oxygenator of claim 12, wherein the manifold divider is disposed in a manifold which receives the stripping gas from the stripping gas inlet and the oxygenation gas from the oxygenation gas inlet, wherein the manifold is open to an entire gas inlet side of the oxygenation fiber bundle and placement of the manifold divider controls an inlet area of the stripping region that receives the stripping gas from the stripping gas inlet and an inlet area of the oxygenation region that receives the oxygenation gas from the oxygenation gas inlet.

14. The blood oxygenator of claim 13, wherein the manifold divider is moveable.

15. The blood oxygenator of claim 14, wherein the manifold divider is fixed.

16. The blood oxygenator of claim 1, wherein the oxygenation fiber bundle further comprises an upper potting and a lower potting, wherein the manifold is located within the housing adjacent to one of the pottings.

17. The blood oxygenator of claim 1, further comprising a blood pump connected to said blood inlet, an oxygenation gas source connected to the oxygenation gas inlet and a stripping gas source connected to the stripping gas inlet.

18. A method for oxygenating blood comprising:
   providing a blood oxygenator having (1) a housing with a blood inlet, a blood outlet, a stripping gas inlet, an oxygenation gas inlet, and at least one gas outlet and (2) an oxygenator fiber bundle disposed within the housing;
   flowing blood through the blood inlet, through the oxygenator fiber bundle, and out the blood outlet;
   flowing a stripping gas through the stripping gas inlet and an oxygenation gas through the oxygenation gas inlet, wherein the stripping gas flows through a stripping region of the oxygenator fiber bundle to the at least one gas outlet and the oxygenation gas through an oxygenation region of the oxygenator fiber bundle to the at least one gas outlet;

wherein the stripping gas region of the oxygenator fiber bundle is upstream of the oxygenation region of the oxygenator fiber bundle.

19. The method of claim 18, wherein the blood travels through the stripping region of the oxygenator fiber bundle in an annular flow path.

20. The method of claim 19, wherein the blood travels through the oxygenation region of the oxygenator fiber bundle in a radially inward flow path.

21. The method of claim 19, wherein the blood travels through the stripping region and the oxygenation region of the oxygenator fiber bundle in a straight direction.

22. The method of claim 18, wherein the blood travels through the oxygenator fiber bundle in a substantially uniform blood flow distribution.

23. The method of claim 18, wherein the fiber bundle has a cross-sectional area and the stripping region that receives the stripping gas from the stripping gas inlet has an inlet area that comprises from 20% to 80% of the cross-sectional area and the oxygenation region that receives the oxygenation gas from the oxygenation gas inlet has an inlet area that comprises from 80% to 20% of the cross-sectional area.

24. The method of claim 23, further comprising moving a manifold divider which directs the stripping gas from the stripping gas inlet to the stripping region of the oxygenator fiber bundle and directs the oxygenation gas from the oxygenation gas inlet to the oxygenation region of the oxygenator fiber bundle to adjust relative areas of the stripping region and the oxygenation region of the oxygenation fiber bundle.

* * * * *